US012427300B1

(12) United States Patent
Gross et al.

(10) Patent No.: US 12,427,300 B1
(45) Date of Patent: *Sep. 30, 2025

(54) PULSATILE VENTRICULAR ASSIST DEVICES

(71) Applicants: Yossi Gross, Moshav Mazor (IL); Oz Cabiri, Hod HaSharon (IL)

(72) Inventors: Yossi Gross, Moshav Mazor (IL); Oz Cabiri, Hod HaSharon (IL)

( * ) Notice: Subject to any disclaimer, the term of this patent is extended or adjusted under 35 U.S.C. 154(b) by 0 days.

This patent is subject to a terminal disclaimer.

(21) Appl. No.: 19/039,635

(22) Filed: Jan. 28, 2025

Related U.S. Application Data

(63) Continuation-in-part of application No. 18/795,359, filed on Aug. 6, 2024.

(51) Int. Cl.
*A61M 60/216* (2021.01)
*A61M 60/126* (2021.01)
(Continued)

(52) U.S. Cl.
CPC ........ *A61M 60/569* (2021.01); *A61M 60/178* (2021.01); *A61M 60/232* (2021.01);
(Continued)

(58) Field of Classification Search
CPC ........ A61M 60/148; A61M 2205/8243; A61M 60/178; A61M 60/232; A61M 60/894;
(Continued)

(56) References Cited

U.S. PATENT DOCUMENTS

| 3,585,983 A | 6/1971 | Kantrowitz et al. |
| 3,842,440 A | 10/1974 | Karlson |

(Continued)

FOREIGN PATENT DOCUMENTS

| WO | WO-2005037348 A1 * | 4/2005 | .......... A61M 1/1005 |
| WO | 2008/141325 A1 | 11/2008 | |

OTHER PUBLICATIONS

Javier Castrodeza et al., "Continuous-flow left ventricular assist device: Current knowledge, complications, and future directions", Cardiology Journal, 2022, vol. 29, No. 2, pp. 293-304 (12 pages total).

(Continued)

*Primary Examiner* — Jon Eric C Morales
(74) *Attorney, Agent, or Firm* — Sughrue Mion, PLLC

(57) ABSTRACT

An implantable LVAD system includes an implantable LVAD including an outflow cannula, which is couplable in fluid communication with a circulatory system of the patient at a first site; and an inflow cannula, which is couplable in fluid communication with the circulatory system at a second site upstream of the first site. The LVAD further includes a continuous-flow pump includes a first inlet in fluid communication with the inflow cannula, and a first outlet. The LVAD still further includes a pulsatile-flow pump includes a second inlet in fluid communication with the first outlet of the continuous-flow pump, and a second outlet in fluid communication with the outflow cannula. Control circuitry is configured to activate the continuous-flow pump to provide flow without synchronization with cardiac cycles of a heart of the patient, and activate the pulsatile-flow pump to provide pulsatile flow synchronized with the cardiac cycles. Other embodiments are also described.

20 Claims, 13 Drawing Sheets

(51) Int. Cl.
  *A61M 60/178* (2021.01)
  *A61M 60/232* (2021.01)
  *A61M 60/258* (2021.01)
  *A61M 60/419* (2021.01)
  *A61M 60/462* (2021.01)
  *A61M 60/531* (2021.01)
  *A61M 60/569* (2021.01)
  *A61M 60/859* (2021.01)
  *A61M 60/88* (2021.01)
  *A61M 60/894* (2021.01)

(52) U.S. Cl.
  CPC ........ *A61M 60/258* (2021.01); *A61M 60/419* (2021.01); *A61M 60/462* (2021.01); *A61M 60/531* (2021.01); *A61M 60/859* (2021.01); *A61M 60/88* (2021.01); *A61M 60/894* (2021.01)

(58) Field of Classification Search
  CPC ........ A61M 2205/3303; A61M 60/152; A61M 60/237; A61M 60/422; A61M 60/462; A61M 60/508; A61M 60/515; A61M 60/554; A61M 60/562; A61M 1/3653; A61M 1/3659; A61M 2205/33; A61M 2205/3365; A61M 2205/3507; A61M 2205/3523; A61M 2205/50; A61M 2205/52; A61M 2205/8206; A61M 2230/04; A61M 2230/06; A61M 60/117; A61M 60/139; A61M 60/196; A61M 60/216; A61M 60/258; A61M 60/268; A61M 60/274; A61M 60/33; A61M 60/414; A61M 60/419; A61M 60/438; A61M 60/441; A61M 60/446; A61M 60/449; A61M 60/531; A61M 60/538; A61M 60/546; A61M 60/569; A61M 60/585; A61M 60/806; A61M 60/861; A61M 60/873; A61M 60/876; A61M 60/896; F04B 17/044; F04B 17/046; A61B 5/029; A61B 5/283; A61B 5/316; A61B 5/363
  See application file for complete search history.

(56) References Cited

U.S. PATENT DOCUMENTS

| | | | |
|---|---|---|---|
| 3,866,604 A | 2/1975 | Curless et al. | |
| 4,102,610 A | 7/1978 | Taboada et al. | |
| 4,210,409 A * | 7/1980 | Child | A61M 60/508 417/241 |
| 4,240,409 A | 12/1980 | Robinson et al. | |
| 4,245,622 A | 1/1981 | Hutchins, IV | |
| 4,375,941 A * | 3/1983 | Child | A61M 60/508 417/418 |
| 4,583,523 A | 4/1986 | Kleinke et al. | |
| 4,610,658 A | 9/1986 | Buchwald et al. | |
| 4,630,597 A | 12/1986 | Kantrowitz et al. | |
| 4,809,676 A | 3/1989 | Freeman | |
| 4,938,766 A | 7/1990 | Jarvik | |
| 5,346,476 A | 9/1994 | Elson | |
| 5,466,221 A | 11/1995 | Zadini et al. | |
| 5,514,079 A | 5/1996 | Dillon et al. | |
| 5,527,159 A | 6/1996 | Bozeman, Jr. et al. | |
| 5,554,103 A | 9/1996 | Zheng et al. | |
| 5,676,651 A * | 10/1997 | Larson, Jr. | A61M 60/237 604/33 |
| 5,693,091 A | 12/1997 | Larson, Jr. et al. | |
| 5,762,599 A | 6/1998 | Sohn | |
| 6,030,336 A | 2/2000 | Franchi | |
| 6,057,689 A | 5/2000 | Saadat | |
| 6,132,363 A | 10/2000 | Freed et al. | |
| 6,200,260 B1 | 3/2001 | Bolling | |
| 6,223,648 B1 | 5/2001 | Erickson | |
| 6,387,037 B1 | 5/2002 | Bolling et al. | |
| 6,390,969 B1 | 5/2002 | Bolling et al. | |
| 6,406,422 B1 | 6/2002 | Landesberg | |
| 6,428,464 B1 | 8/2002 | Bolling | |
| 6,450,942 B1 | 9/2002 | Lapanashvili et al. | |
| 6,468,200 B1 | 10/2002 | Fischi | |
| 6,511,413 B2 | 1/2003 | Landesberg | |
| 6,540,699 B1 | 4/2003 | Smith | |
| 6,572,652 B2 | 6/2003 | Shaknovich | |
| 6,685,621 B2 | 2/2004 | Bolling et al. | |
| 6,808,484 B1 | 10/2004 | Peters et al. | |
| 6,984,201 B2 | 1/2006 | Khaghani et al. | |
| 7,229,258 B2 | 6/2007 | Wood et al. | |
| 7,544,160 B2 | 6/2009 | Gross | |
| 7,811,221 B2 | 10/2010 | Gross | |
| 8,690,749 B1 | 4/2014 | Nunez | |
| 9,517,129 B2 | 12/2016 | Wilson et al. | |
| 10,568,999 B2 | 2/2020 | Gross | |
| 11,013,906 B2 | 5/2021 | Gross | |
| 11,395,910 B2 | 7/2022 | Gross | |
| 11,565,104 B1 | 1/2023 | Gross | |
| 2002/0103413 A1 | 8/2002 | Bugge et al. | |
| 2002/0151761 A1 | 10/2002 | Viole et al. | |
| 2002/0173735 A1 | 11/2002 | Lewis | |
| 2003/0032853 A1 | 2/2003 | Korakianitis et al. | |
| 2003/0163020 A1 | 8/2003 | Frazier | |
| 2006/0217588 A1 * | 9/2006 | Gross | A61M 60/268 600/16 |
| 2010/0298929 A1 | 11/2010 | Thornton et al. | |
| 2011/0029072 A1 | 2/2011 | Gabbay | |
| 2011/0037327 A1 | 2/2011 | Denne | |
| 2016/0151553 A1 * | 6/2016 | Bonde | A61M 60/538 455/411 |
| 2016/0206798 A1 | 7/2016 | Williams et al. | |
| 2017/0112985 A1 * | 4/2017 | Yomtov | A61B 5/316 |
| 2021/0252272 A1 | 8/2021 | Slavinski et al. | |

OTHER PUBLICATIONS

Letsou GV, Pate TD, Gohean JR, Kurusz M, Longoria RG, Kaiser L, Smalling RW. Improved left ventricular unloading and circulatory support with synchronized pulsatile left ventricular assistance compared with continuous-flow left ventricular assistance in an acute porcine left ventricular failure model. J Thorac Cardiovasc Surg. Nov. 2010;140(5):1181-8. doi: 10.1016/j.jtcvs.2010.03.043. Epub May 23, 2010. PMID: 20546799.
Voice coil actuators vs solenoid—- What is the difference— Aerospace Manufacturing and Design Oct. 28, 2015.
Office Action dated Oct. 15, 2024, which issued during the prosecution of U.S. Appl. No. 18/795,359.
Final Office Action dated Feb. 4, 2025, which issued during the prosecution of U.S. Appl. No. 18/795,359.
Medtronic Press Release, New Study Demonstrates Feasibility of Novel Mechanical Sensor in Medtronic Micra Transcatheter Pacing System to Detect Atrial Contractions and Restore AV Synchrony, May 11, 2018.

* cited by examiner

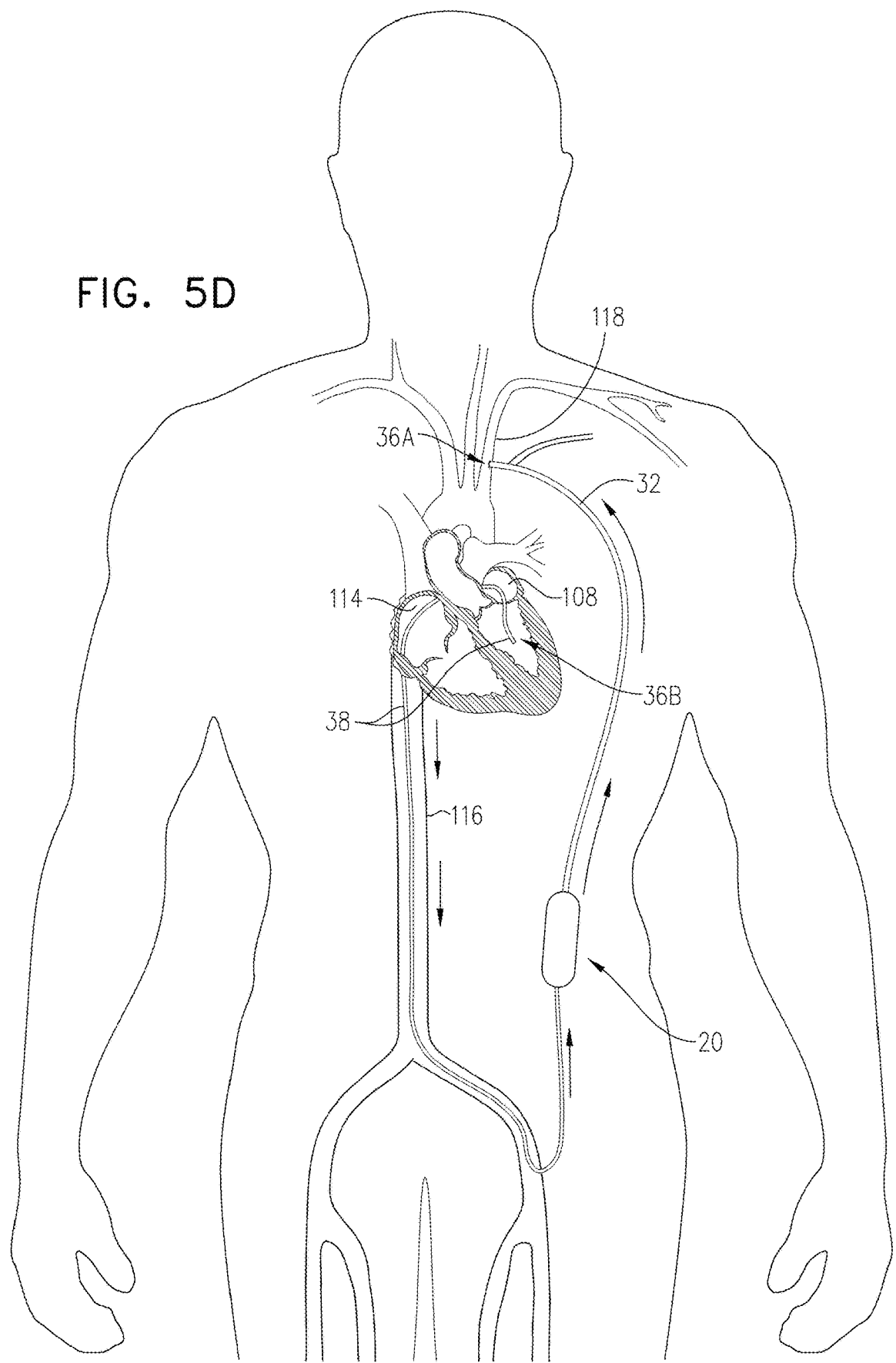

PULSATILE VENTRICULAR ASSIST DEVICES

CROSS-REFERENCE TO RELATED APPLICATIONS

The present application claims priority from and is a continuation-in-part (CIP) of U.S. application Ser. No. 18/795,359, filed Aug. 6, 2024, which is incorporated herein by reference.

FIELD OF THE APPLICATION

The present invention relates generally to left ventricular assist devices (LVADs), and specifically to pulsatile LVADs.

BACKGROUND OF THE APPLICATION

A left ventricular assist device (LVAD) is an electromechanical device that helps pump blood from the left ventricle to partially or to completely replace the function of a failing heart. The two main types of LVADs are pulsatile LVADs and continuous-flow LVADs, also known as nonpulsatile LVADs. Pulsatile LVADs mimic the natural rhythmic action of the heart, while continuous-flow LVADs use a motor at fixed velocities, leading to nearly constant pressure in the ascending aorta, i.e., minimal pulsatility.

As a consequence, continuous-flow LVADs are associated with substantial side effects, including:
  altered arterial baroreceptors-reduced pulsatility leads to increased sympathetic activation and peripheral vascular resistance;
  increased cardiovascular risk factors, which include essential hypertension, stroke, chronic kidney disease, and reduced likelihood of myocardial recovery;
  increased aortic leaflet strain, which may cause aortic valve issues like fusion and regurgitation;
  gastrointestinal bleeding, which is common due to lack of pulsatility and enhanced proteolysis;
  reduced blood pressure control, which is crucial for maintaining flow and cardiac output; and
  blood pressure measurement challenges, because standard methods are less effective without pulsatile flow.

In addition, continuous-flow LVAD malfunction can result in death.

U.S. Pat. No. 11,565,104 to Gross describes a mechanical circulatory assist device that includes a stent, a coiled wire wound around the stent, and a reciprocating valve including a housing, one or more leaflets coupled to the housing, and one or more permanent magnets coupled to the housing. The magnets are arranged to interact with a magnetic field generated by the coiled wire when current flows therethrough, so as to axially move the reciprocating valve with respect to the stent when the reciprocating valve is disposed within the stent. Upstream axial motion of the reciprocating valve causes the leaflets to be in an open state in which they allow blood flow through the reciprocating valve. Downstream axial motion of the reciprocating valve causes the leaflets to be in a closed state in which they inhibit blood flow through the reciprocating valve. Other embodiments are also described.

U.S. Pat. No. 10,568,999 to Gross describes apparatus for deployment in a lumen of a blood vessel of a subject. The apparatus includes a reciprocating device configured to move downstream and upstream in the blood vessel in a reciprocating pattern to provide: (i) a first effective surface area of the device for pushing blood downstream in the blood vessel during downstream motion of the reciprocating device, and (ii) second effective surface area of the during upstream motion of the reciprocating device. The first effective surface area is larger for pushing blood in the blood vessel than the second effective surface area. The apparatus further includes a device driver configured to drive the reciprocating device in the reciprocating pattern. Other applications are also described.

PCT Publication WO 2004/073484 to Gross et al. describes apparatus that includes an inflatable bladder, adapted to be coupled to a blood vessel of a subject carrying oxygenated blood, such that an interior of the bladder is in fluid communication with the blood. The apparatus also includes a piston in mechanical communication with the bladder; a motor, adapted to synchronize contraction and expansion of the bladder with a cardiac cycle of the subject by applying a motor force to the piston; and a spring, adapted to apply a spring force to the piston.

U.S. Pat. No. 5,693,091 to Larson, Jr. et al. describes, in one embodiment, a surgically implantable reciprocating pump that employs a check valve as the piston, which is driven by a permanent magnet linear electric motor to assist either side of the natural heart. The pump is implanted in the aorta or pulmonary artery using vascular attachment cuffs such as flexible cuffs for suturing at each end with the pump output directly in line with the artery. The pump is powered by surgically implanted rechargeable batteries. In another embodiment, pairs of pumps are provided to replace or assist the natural heart or to provide temporary blood flow throughout the body, for example, during operations to correct problems with the natural heart.

SUMMARY OF THE APPLICATION

Some embodiments of the present invention provide a left ventricular assist device (LVAD) system for treating a patient. The LVAD system comprises an implantable LVAD for implantation in the patient. The implantable LVAD comprises a pump, which is shaped so as to define a pump chamber having an upstream inflow end and a downstream outflow end. The pump comprises a tubular linear motor comprising a magnetic piston and a stator. The magnetic piston comprises a reciprocating one-way valve configured to allow downstream blood flow and inhibit upstream blood flow. The stator is configured to magnetically drive the magnetic piston with reciprocating motion, so as to pump blood downstream during downstream motion of the magnetic piston while the reciprocating one-way valve is closed. The pump further comprises a spring, which is arranged to store energy during upstream motion of the magnetic piston and release the stored energy during the downstream motion of the magnetic piston.

The LVAD further comprises outflow and inflow cannulas. The outflow cannula is couplable in fluid communication with a circulatory system of the patient at a first site, and arranged in fluid communication with the downstream outflow end of the pump chamber via a stationary one-way outflow valve of the LVAD. The stationary one-way outflow valve is configured to allow downstream blood flow from the pump chamber to the outflow cannula and to inhibit upstream blood flow from the outflow cannula to the pump chamber. The inflow cannula is couplable in fluid communication with the circulatory system at a second site upstream of the first site, and arranged to allow downstream blood flow from the inflow cannula to the upstream inflow end of the pump chamber.

The LVAD system further comprises a cardiac sensor and control circuitry. The cardiac sensor is configured to sense one or more features of a plurality of cardiac cycles of the heart. The control circuitry is coupled to the cardiac sensor and configured to activate the tubular linear motor to provide pulsatile flow synchronized with the cardiac cycles by, during each of the cardiac cycles:

activating the stator of the tubular linear motor, during at least a portion of systole, to move the magnetic piston downstream during a first period of time, and activating the stator of the tubular linear motor, during at least a portion of diastole, to move the magnetic piston upstream during a second period of time.

The motion of the magnetic piston upstream during the second period stores energy in the spring, which releases the stored energy during systole, thereby reducing the amount of energy that the tubular linear motor must apply during systole in order to achieve a given amount of downstream motion of the magnetic piston. This allocation of activation of the tubular linear motor between diastole and systole reduces the peak power consumed by the tubular linear motor during systole, which may reduce the motor's demands on a power source (e.g., comprising one or more batteries) of the LVAD system. For example, the control circuitry and the spring may be configured such that, during each of the cardiac cycles, peak power consumed by the tubular linear motor during systole is no more than three times, such as no more than two times, peak power consumed by the tubular linear motor during diastole.

The activation of the tubular linear motor to pump blood downstream only during a portion of systole provides pulsatile blood flow, which mimics the healthy heart's natural function. Pulsatility in blood flow is considered crucial for normal organ function, particularly for critical organs such as the kidney, liver, brain, and heart.

In an application of the present invention, the control circuitry is configured to activate the tubular linear motor to provide pulsatile flow synchronized with the cardiac cycles by:

during at least a portion of systole of each of the cardiac cycles, activating the stator of the tubular linear motor to move the magnetic piston downstream at a velocity set based on a target stroke volume and a target stroke duration, and during at least a portion of diastole of each of the cardiac cycles, activating the stator of the tubular linear motor to move the magnetic piston upstream.

Thus, the control circuitry uses the target stroke volume and target stroke duration as inputs to calculate the velocity of the magnetic piston, such that the magnetic piston moves during the entirety of the target stroke duration, rather than moving the magnetic piston at a predetermined rate for the amount of time necessary to provide the target stroke volume. Utilizing the entire available target stroke duration may reduce peak energy consumption and/or provide pumping that more closely mimics the natural physiological pumping.

Some embodiments of the present invention provide another LVAD system for treating a patient. This LVAD system may optionally implement any of the features of the LVAD system described hereinabove. An LVAD of this LVAD system comprises a continuous-flow pump and a pulsatile-flow pump. The continuous-flow pump comprises a first inlet in fluid communication with inflow cannula, and a first outlet. The pulsatile-flow pump comprises a second inlet, and a second outlet, which is in fluid communication with the outflow cannula. The second inlet of the pulsatile-flow pump is in fluid communication with the first outlet of the continuous-flow pump, and thus with the inflow cannula via the continuous-flow pump. The inflow cannula is therefore arranged to allow downstream blood flow from the inflow cannula to the second inlet. The pulsatile-flow pump may implement any of the features of the pulsatile-flow pump described hereinabove, mutatis mutandis.

The control circuitry of the LVAD system is configured to:
activate the continuous-flow pump to provide flow without synchronization with cardiac cycles of a heart of the patient, and
activate the pulsatile-flow pump to provide pulsatile flow synchronized with the cardiac cycles.

There is therefore provided, in accordance with an application of the present invention, a left ventricular assist device (LVAD) system for treating a patient, the LVAD system including:

(i) an implantable LVAD for implantation in the patient, the LVAD including:
  (a) an outflow cannula, which is couplable in fluid communication with a circulatory system of the patient at a first site;
  (b) an inflow cannula, which is couplable in fluid communication with the circulatory system at a second site upstream of the first site;
  (c) a continuous-flow pump, which includes (1) a first inlet in fluid communication with the inflow cannula, and (2) a first outlet; and
  (d) a pulsatile-flow pump, which includes (1) a second inlet in fluid communication with the first outlet of the continuous-flow pump, and (2) a second outlet in fluid communication with the outflow cannula; and (ii) control circuitry, which is configured to:
  activate the continuous-flow pump to provide flow without synchronization with cardiac cycles of a heart of the patient, and
  activate the pulsatile-flow pump to provide pulsatile flow synchronized with the cardiac cycles.

For some applications, the LVAD further includes a cardiac sensor, which is configured to sense one or more features of the cardiac cycles, and the control circuitry is coupled to the cardiac sensor.

For some applications, the second site is an apex of a left ventricle of the heart.

For some applications, the LVAD further includes a stationary one-way outflow valve, which is arranged to allow downstream blood flow from the second outlet of the pulsatile-flow pump to the outflow cannula, and to inhibit upstream blood flow from the outflow cannula to the second outlet.

For some applications, the LVAD further includes a tube which couples the second inlet of the pulsatile-flow pump in the fluid communication with the first outlet of the continuous-flow pump.

For any of the applications described above, the pulsatile-flow pump may:
  be shaped so as to define a pump chamber having (a) an upstream inflow end in fluid communication with the second inlet, and (b) a downstream outflow end in fluid communication with the second outlet, and
  include a tubular linear motor, which includes (a) a magnetic piston, which includes a reciprocating one-way valve configured to allow downstream blood flow and inhibit upstream blood flow; and (b) a stator, which is configured to magnetically drive the magnetic piston with reciprocating motion, so as to pump blood downstream during downstream motion of the magnetic piston while the reciprocating one-way valve is closed.

For some applications, the control circuitry is configured to activate the tubular linear motor to provide the pulsatile flow synchronized with the cardiac cycles by, during each of the cardiac cycles:
  activating the stator of the tubular linear motor to move the magnetic piston downstream during a portion of systole of the cardiac cycle, and
  activating the stator of the tubular linear motor to move the magnetic piston upstream during at least a portion of diastole of the cardiac cycle.

For some applications, the LVAD further includes a stationary one-way outflow valve, which is arranged to allow downstream blood flow from the second outlet of the pulsatile-flow pump to the outflow cannula, and to inhibit upstream blood flow from the outflow cannula to the second outlet.

For some applications, the LVAD further includes a stationary one-way inflow valve, which is arranged to allow downstream blood flow into the pump chamber of the pulsatile-flow pump, and to inhibit upstream blood flow from the pump chamber.

For any of the applications described above, the continuous-flow pump may be a magnetically-levitated centrifugal pump.

For any of the applications described above, the control circuitry may be configured to activate the pulsatile-flow pump to provide pulsatile flow synchronized with the cardiac cycles by, during each of the cardiac cycles, activating the pulsatile-flow pump to pump blood downstream during a portion of systole of the cardiac cycle.

For some applications, the control circuitry is configured to activate the pulsatile-flow pump to pump blood downstream during the portion of systole of the cardiac cycle, and not to pump blood downstream during any portion of diastole of the cardiac cycle.

For some applications, the control circuitry is configured, during each of the cardiac cycles, to activate the pulsatile-flow pump to begin the portion of systole at a delay after the beginning of systole.

For some applications, a duration of the delay is 200-400 milliseconds, such as 300-400 milliseconds.

For some applications:
  the LVAD system further includes a cardiac sensor, which is configured to sense one or more features of the cardiac cycles,
  the control circuitry is coupled to the cardiac sensor, and
  the control circuitry is configured to set a duration of the delay equal to 20%-40% of a total duration of the cardiac cycle.

For some applications, the control circuitry is configured to activate the pulsatile-flow pump to begin the portion of systole upon detection by the control circuitry of a beginning of a decline in pressure after a rise in pressure during systole.

For some applications:
  the pulsatile-flow pump:
    is shaped so as to define a pump chamber having (a) an upstream inflow end in fluid communication with the second inlet, and (b) a downstream outflow end in fluid communication with the second outlet, and
    includes a tubular linear motor, which includes (a) a magnetic piston, which includes a reciprocating one-way valve configured to allow downstream blood flow and inhibit upstream blood flow; and (b) a stator, which is configured to magnetically drive the magnetic piston with reciprocating motion, so as to pump blood downstream during downstream motion of the magnetic piston while the reciprocating one-way valve is closed,
  the LVAD system further includes an upstream pressure sensor, which is disposed and configured to measure blood pressure of blood upstream of the magnetic piston of the pulsatile-flow pump, and
  the control circuitry is configured to detect the beginning of the decline in the pressure after the rise in the pressure during systole, using the upstream pressure sensor.

For some applications, the upstream pressure sensor is disposed and configured to measure the blood pressure of blood entering the upstream inflow end of the pump chamber of the pulsatile-flow pump.

For some applications, the upstream pressure sensor is disposed upstream of the continuous-flow pump, and configured to measure left-ventricular pressure (LVP).

There is further provided, in accordance with an application of the present invention, a method for treating a patient including:
  implanting a left ventricular assist device (LVAD) of an LVAD system in the patient, by:
    coupling an outflow cannula of the LVAD in fluid communication with a circulatory system of the patient at a first site; and
    coupling an inflow cannula of the LVAD in fluid communication with the circulatory system at a second site upstream of the first site,
    wherein the LVAD includes (a) a continuous-flow pump, which includes (1) a first inlet in fluid communication with the inflow cannula, and (2) a first outlet, and (b) a pulsatile-flow pump, which includes (1) a second inlet in fluid communication with the first outlet of the continuous-flow pump, and (2) a second outlet in fluid communication with the outflow cannula; and
  activating control circuitry of the LVAD system to:
    activate the continuous-flow pump to provide flow without synchronization with cardiac cycles of a heart of the patient, and
    activate the pulsatile-flow pump to provide pulsatile flow synchronized with the cardiac cycles.

For some applications, the LVAD system further includes a cardiac sensor, which is configured to sense one or more features of the cardiac cycles, and the control circuitry is coupled to the cardiac sensor.

For some applications, the LVAD system further includes a stationary one-way outflow valve, which is arranged to allow downstream blood flow from the second outlet of the pulsatile-flow pump to the outflow cannula, and to inhibit upstream blood flow from the outflow cannula to the second outlet.

For some applications, the LVAD system further includes a tube which couples the second inlet of the pulsatile-flow pump in the fluid communication with the first outlet of the continuous-flow pump.

For some applications, the pulsatile-flow pump:
  is shaped so as to define a pump chamber having (a) an upstream inflow end in fluid communication with the second inlet, and (b) a downstream outflow end in fluid communication with the second outlet, and
  includes a tubular linear motor, which includes (a) a magnetic piston, which includes a reciprocating one-way valve configured to allow downstream blood flow and inhibit upstream blood flow; and (b) a stator, which is configured to magnetically drive the magnetic piston with reciprocating motion, so as to pump blood downstream during downstream motion of the magnetic piston while the reciprocating one-way valve is closed.

For some applications, activating the control circuitry includes activating the control circuitry to activate the tubular linear motor to provide the pulsatile flow synchronized with the cardiac cycles by, during each of the cardiac cycles:
  activating the stator of the tubular linear motor to move the magnetic piston downstream during a portion of systole of the cardiac cycle, and
  activating the stator of the tubular linear motor to move the magnetic piston upstream during at least a portion of diastole of the cardiac cycle.

For some applications, the LVAD system further includes a stationary one-way outflow valve, which is arranged to allow downstream blood flow from the second outlet of the pulsatile-flow pump to the outflow cannula, and to inhibit upstream blood flow from the outflow cannula to the second outlet.

For some applications, the LVAD system further includes a stationary one-way inflow valve, which is arranged to allow downstream blood flow into the pump chamber of the pulsatile-flow pump, and to inhibit upstream blood flow from the pump chamber.

For some applications, the continuous-flow pump includes a magnetically-levitated centrifugal pump.

For some applications, activating the control circuitry includes activating the control circuitry to activate the pulsatile-flow pump to provide pulsatile flow synchronized with the cardiac cycles by, during each of the cardiac cycles, activating the pulsatile-flow pump to pump blood downstream during a portion of systole of the cardiac cycle.

For some applications, activating the control circuitry includes activating the control circuitry to activate the pulsatile-flow pump to pump blood downstream during the portion of systole of the cardiac cycle, and not to pump blood downstream during any portion of diastole of the cardiac cycle.

For some applications, activating the control circuitry includes activating the control circuitry to, during each of the cardiac cycles, activate the pulsatile-flow pump to begin the portion of systole at a delay after the beginning of systole.

For some applications, a duration of the delay is 200-400 milliseconds, such as 300-400 milliseconds.

For some applications:
  the LVAD system further includes a cardiac sensor, which is configured to sense one or more features of the cardiac cycles,
  the control circuitry is coupled to the cardiac sensor, and activating the control circuitry includes activating the control circuitry to set a duration of the delay equal to 20%-40% of a total duration of the cardiac cycle.

For some applications, activating the control circuitry includes activating the control circuitry to activate the pulsatile-flow pump to begin the portion of systole upon detection by the control circuitry of a beginning of a decline in pressure after a rise in pressure during systole.

For some applications:
  the pulsatile-flow pump:
    is shaped so as to define a pump chamber having (a) an upstream inflow end in fluid communication with the second inlet, and (b) a downstream outflow end in fluid communication with the second outlet, and includes a tubular linear motor, which includes (a) a magnetic piston, which includes a reciprocating one-way valve configured to allow downstream blood flow and inhibit upstream blood flow; and (b) a stator, which is configured to magnetically drive the magnetic piston with reciprocating motion, so as to pump blood downstream during downstream motion of the magnetic piston while the reciprocating one-way valve is closed,
  the LVAD system further includes an upstream pressure sensor, which is disposed and configured to measure blood pressure of blood upstream of the magnetic piston of the pulsatile-flow pump, and
  activating the control circuitry includes activating the control circuitry to detect the beginning of the decline in the pressure after the rise in the pressure during systole, using the upstream pressure sensor.

For some applications, the upstream pressure sensor is disposed and configured to measure the blood pressure of blood entering the upstream inflow end of the pump chamber of the pulsatile-flow pump.

For some applications, the upstream pressure sensor is disposed upstream of the continuous-flow pump, and configured to measure left-ventricular pressure (LVP).

For some applications:
  the second site is an apex of a left ventricle of the heart, and
  implanting the LVAD includes coupling the inflow cannula of the LVAD in fluid communication with the circulatory system at the apex of the left ventricle.

There is still further provided, in accordance with an application of the present invention, a left ventricular assist device (LVAD) system for treating a patient, the LVAD system including:
  (i) an implantable LVAD for implantation in the patient, the LVAD including a pump, which (a) is shaped so as to define a pump chamber having an upstream inflow end and a downstream outflow end, and (b) includes:
    a tubular linear motor, which includes (1) a magnetic piston, which includes a reciprocating one-way valve configured to allow downstream blood flow and inhibit upstream blood flow; and (2) a stator, which is configured to magnetically drive the magnetic piston with reciprocating motion, so as to pump blood downstream during downstream motion of the magnetic piston while the reciprocating one-way valve is closed;
    an outflow cannula, which is (1) couplable in fluid communication with a circulatory system of the patient at a first site, and (2) arranged in fluid communication with the downstream outflow end of the pump chamber; and
    an inflow cannula, which is (1) couplable in fluid communication with the circulatory system at a second site upstream of the first site, and (2) arranged to allow downstream blood flow from the inflow cannula to the upstream inflow end of the pump chamber;
  (ii) a cardiac sensor, configured to sense one or more features of a plurality of cardiac cycles of a heart of the patient; and
  (iii) control circuitry, which is coupled to the cardiac sensor and configured to activate the tubular linear motor to provide pulsatile flow synchronized with the cardiac cycles by, during each of the cardiac cycles:
    activating the stator of the tubular linear motor to move the magnetic piston downstream during a portion of systole of the cardiac cycle, the portion beginning at a delay after the beginning of systole, and activating the stator of the tubular linear motor to move the magnetic piston upstream during at least a portion of diastole of the cardiac cycle.

For some applications, a duration of the delay is 200-400 milliseconds, such as 300-400 milliseconds.

For some applications, the control circuitry is configured to set a duration of the delay equal to 20%-40% of a total duration of the cardiac cycle.

For some applications, the control circuitry is configured to activate the pulsatile-flow pump to begin the portion of systole upon detection by the control circuitry of a beginning of a decline in pressure after a rise in pressure during systole.

For some applications:
the LVAD system further includes an upstream pressure sensor, which is disposed and configured to measure blood pressure of blood upstream of the magnetic piston of the pulsatile-flow pump, and
the control circuitry is configured to detect the beginning of the decline in the pressure after the rise in the pressure during systole, using the upstream pressure sensor.

For some applications, the upstream pressure sensor is disposed and configured to measure the blood pressure of blood entering the upstream inflow end of the pump chamber of the pulsatile-flow pump.

For some applications, the upstream pressure sensor is disposed and configured to measure left-ventricular pressure (LVP).

For some applications, the apparatus further includes a stationary one-way outflow valve, which is configured to allow downstream blood flow from the pump chamber to the outflow cannula and to inhibit upstream blood flow from the outflow cannula to the pump chamber.

There is additionally provided, in accordance with an application of the present invention, a left ventricular assist device (LVAD) system for treating a patient, the LVAD system including:
(i) an implantable LVAD for implantation in the patient, the LVAD including:
a stationary one-way outflow valve; and
a pump, which (a) is shaped so as to define a pump chamber having an upstream inflow end and a downstream outflow end, and (b) includes:
a tubular linear motor, which includes (1) a magnetic piston, which includes a reciprocating one-way valve configured to allow downstream blood flow and inhibit upstream blood flow; and (2) a stator, which is configured to magnetically drive the magnetic piston with reciprocating motion, so as to pump blood downstream during downstream motion of the magnetic piston while the reciprocating one-way valve is closed;
a spring, which is arranged to store energy during upstream motion of the magnetic piston and release the stored energy during the downstream motion of the magnetic piston;
an outflow cannula, which is (1) couplable in fluid communication with a circulatory system of the patient at a first site, and (2) arranged in fluid communication with the downstream outflow end of the pump chamber via the stationary one-way outflow valve, wherein the stationary one-way outflow valve is configured to allow downstream blood flow from the pump chamber to the outflow cannula and to inhibit upstream blood flow from the outflow cannula to the pump chamber; and an inflow cannula, which is (1) couplable in fluid communication with the circulatory system at a second site upstream of the first site, and (2) arranged to allow downstream blood flow from the inflow cannula to the upstream inflow end of the pump chamber;
(ii) a cardiac sensor, configured to sense one or more features of a plurality of cardiac cycles of a heart of the patient; and
(iii) control circuitry, which is coupled to the cardiac sensor and configured to activate the tubular linear motor to provide pulsatile flow synchronized with the cardiac cycles by, during each of the cardiac cycles:
activating the stator of the tubular linear motor, during a first portion of the cardiac cycle, to move the magnetic piston downstream during a first period of time, and
activating e stator of the tubular linear motor, during a second portion of the cardiac cycle, to move the magnetic piston upstream during a second period of time,
wherein the first portion of the cardiac cycle is at least a portion of one of systole or diastole, and the second portion of the cardiac cycle is at least a portion of the other of systole or diastole.

For some applications, the first period of time has a first duration, and the second period of time has a second duration greater than the first duration.

For some applications, the spring includes an elastic spring.

For some applications, the spring includes a magnetic spring.

For some applications:
the implantable LVAD further includes a stationary one-way inflow valve,
the inflow cannula is arranged to allow the downstream blood flow from the inflow cannula to the upstream inflow end of the pump chamber via the stationary one-way inflow valve, and
the stationary one-way inflow valve is configured to allow downstream blood flow from the inflow cannula to the pump chamber and to inhibit upstream blood flow from the pump chamber to the inflow cannula.

For some applications, the LVAD system further includes a battery arranged to provide power to the tubular linear motor.

For any of the applications described above, the control circuitry and the spring may be configured such that, during each of the cardiac cycles, peak power consumed by the tubular linear motor during the first portion of the cardiac cycle is no more than three times peak power consumed by the tubular linear motor during the second portion of the cardiac cycle. For some of these applications, the control circuitry and the spring are configured such that, during each of the cardiac cycles, the peak power consumed by the tubular linear motor during the first portion of the cardiac cycle is no more than two times the peak power consumed by the tubular linear motor during the second portion of the cardiac cycle.

There is yet additionally provided, in accordance with an application of the present invention, a left ventricular assist device (LVAD) system for treating a patient, the LVAD system including:
(i) an implantable LVAD for implantation in the patient, the LVAD including:
a stationary one-way outflow valve; and a pump, which (a) is shaped so as to define a pump
chamber having an upstream inflow end and a downstream outflow end, and (b) includes:
a tubular linear motor, which includes (1) a magnetic
piston, which includes a reciprocating one-way
valve configured to allow downstream blood flow
and inhibit upstream blood flow; and (2) a stator,
which is configured to magnetically drive the
magnetic piston with reciprocating motion, so as
to pump blood downstream during downstream
motion of the magnetic piston while the reciprocating one-way valve is closed;
an outflow cannula, which is (1) couplable in fluid
communication with a circulatory system of the
patient at a first site, and (2) arranged in fluid
communication with the downstream outflow end
of the pump chamber via the stationary one-way
outflow valve, wherein the stationary one-way
outflow valve is configured to allow downstream
blood flow from the pump chamber to the outflow
cannula and to inhibit upstream blood flow from
the outflow cannula to the pump chamber; and
an inflow cannula, which is (1) couplable in fluid
communication with the circulatory system at a
second site upstream of the first site, and (2)
arranged to allow downstream blood flow from the
inflow cannula to the upstream inflow end of the
pump chamber;
(ii) a cardiac sensor, configured to sense one or more
features of a plurality of cardiac cycles of a heart of the
patient; and
(iii) control circuitry, which is coupled to the cardiac
sensor and configured to activate the tubular linear
motor to provide pulsatile flow synchronized with the
cardiac cycles by:
during a first portion of each of the cardiac cycles,
activating the stator of the tubular linear motor to
move the magnetic piston downstream at a velocity
set based on a target stroke volume and a target
stroke duration, and
during a second portion of each of the cardiac cycles,
activating the stator of the tubular linear motor to
move the magnetic piston upstream,
wherein the first portion of each of the cardiac cycles is
at least a portion of one of systole or diastole, and the
second portion of each of the cardiac cycles is at least
a portion of the other of systole or diastole.

For some applications, the LVAD system further includes
a left atrial pressure sensor, which is configured to sense left
atrial pressure, and the control circuitry is configured to set
the target stroke volume at a level that prevents the sensed
left atrial pressure from exceeding a threshold pressure.

For some applications:
the implantable LVAD further includes a stationary one-way inflow valve,
the inflow cannula is arranged to allow the downstream
blood flow from the inflow cannula to the upstream
inflow end of the pump chamber via the stationary
one-way inflow valve, and
the stationary one-way inflow valve is configured to allow
downstream blood flow from the inflow cannula to the
pump chamber and to inhibit upstream blood flow from
the pump chamber to the inflow cannula.

For some applications, the LVAD system further includes
a battery arranged to provide power to the tubular linear
motor.

For any of the applications described above, the LVAD
system may further include one or more activity sensors,
which are configured to sense a level of activity of the
patient, and the control circuitry may be configured to set the
target stroke volume responsively to the sensed level of
activity of the patient. For some applications, the one or
more activity sensors include an accelerometer, which is
configured to sense the level of activity of the patient. For
some applications, the one or more activity sensors include
a respiration sensor, which is configured to sense the level of
activity of the patient by sensing one or more parameters of
respiration of the patient. For some applications, the respiration sensor is configured to detect transthoracic impedance.

For any of the applications described above, the control
circuitry may be configured to set the target stroke duration
responsively to the sensed one or more features of the
plurality of cardiac cycles. For some applications, the control circuitry is configured to set the target stroke duration
responsively to a duration of systole of the plurality of
cardiac cycles. For some applications, the control circuitry is
configured to set the target stroke duration equal to a fraction
of the duration of systole of the plurality of cardiac cycles.
For some applications, the control circuitry is configured to
set the target stroke duration responsively to a duration of
diastole of the plurality of cardiac cycles. For some applications, the control circuitry is configured to set the target
stroke duration equal to a fraction of the duration of diastole
of the plurality of cardiac cycles.

There is also provided, in accordance with an application
of the present invention, a left ventricular assist device
(LVAD) system for treating a patient, the LVAD system
including:
(i) an implantable LVAD for implantation in the patient,
the LVAD including:
a stationary one-way outflow valve; and
a pump, which (a) is shaped so as to define a pump
chamber having an upstream inflow end and a downstream outflow end, and (b) includes:
a tubular linear motor, which includes (1) a magnetic
piston, which includes a reciprocating one-way
valve configured to allow downstream blood flow
and inhibit upstream blood flow; and (2) a stator,
which is configured to magnetically drive the
magnetic piston with reciprocating motion, so as
to pump blood downstream during downstream
motion of the magnetic piston while the reciprocating one-way valve is closed, wherein an inner
surface of the pump chamber and an outer surface
of the magnetic piston have respective rectangular
cross-sections perpendicular to a central longitudinal axis of the pump chamber;
an outflow cannula, which is (1) couplable in fluid
communication with a circulatory system of the
patient at a first site, and (2) arranged in fluid
communication with the downstream outflow end
of the pump chamber via the stationary one-way
outflow valve, wherein the stationary one-way
outflow valve is configured to allow downstream
blood flow from the pump chamber to the outflow
cannula and to inhibit upstream blood flow from
the outflow cannula to the pump chamber; and
an inflow cannula, which is (1) couplable in fluid
communication with the circulatory system at a
second site upstream of the first site, and (2)

arranged to allow downstream blood flow from the inflow cannula to the upstream inflow end of the pump chamber;

(ii) a cardiac sensor, configured to sense one or more features of a plurality of cardiac cycles of a heart of the patient; and (iii) control circuitry, which is coupled to the cardiac sensor and configured to activate the tubular linear motor to provide pulsatile flow synchronized with the cardiac cycles.

For some applications, the control circuitry is configured to activate the tubular linear motor to provide the pulsatile flow synchronized with the cardiac cycles by:

during a first portion of each of the cardiac cycles, activating the stator of the tubular linear motor to move the magnetic piston downstream, during a second portion of each of the cardiac cycles, activating the stator of the tubular linear motor to move the magnetic piston upstream, wherein the first portion of each of the cardiac cycles is at least a portion of one of systole or diastole, and the second portion of each of the cardiac cycles is at least a portion of the other of systole or diastole.

There is further provided, in accordance with an application of the present invention, a method including:

accessing a thoracic cavity of a patient; and transthoracically implanting a left ventricular assist device (LVAD) in the patient by:

transmurally inserting an inflow cannula of the LVAD into a left atrial appendage (LAA) of a heart, and securing the inflow cannula to a left atrial wall, and anastomosing an outflow cannula of the LVAD to a descending aorta.

For some applications, accessing the thoracic cavity includes performing a left thoracotomy.

For some applications:

inserting the inflow cannula into the LAA includes passing an inflow end opening of the inflow cannula through a mitral valve into a left ventricle, and securing the inflow cannula to the left atrial wall holds the inflow end opening of the inflow cannula in the left ventricle.

For some applications, implanting the LVAD includes identifying that the patient suffers from mitral regurgitation, and passing the inflow end opening of the inflow cannula through the mitral valve into the left ventricle causes leaflets of the mitral valve to at least partially contact an outer surface of the inflow cannula during systole, thereby reducing mitral regurgitation.

For some applications:

inserting the inflow cannula into the LAA includes positioning an inflow end opening of the inflow cannula in a left atrium, and securing the inflow cannula to the left atrial wall holds the inflow end opening of the inflow cannula in the left atrium.

The present invention will be more fully understood from the following detailed description of embodiments thereof, taken together with the drawings, in which:

BRIEF DESCRIPTION OF THE DRAWINGS

FIGS. 5A-D are schematic illustrations of methods of coupling an implantable LVAD in fluid communication with a circulatory system of a patient;

DETAILED DESCRIPTION OF APPLICATIONS

Figure 1:
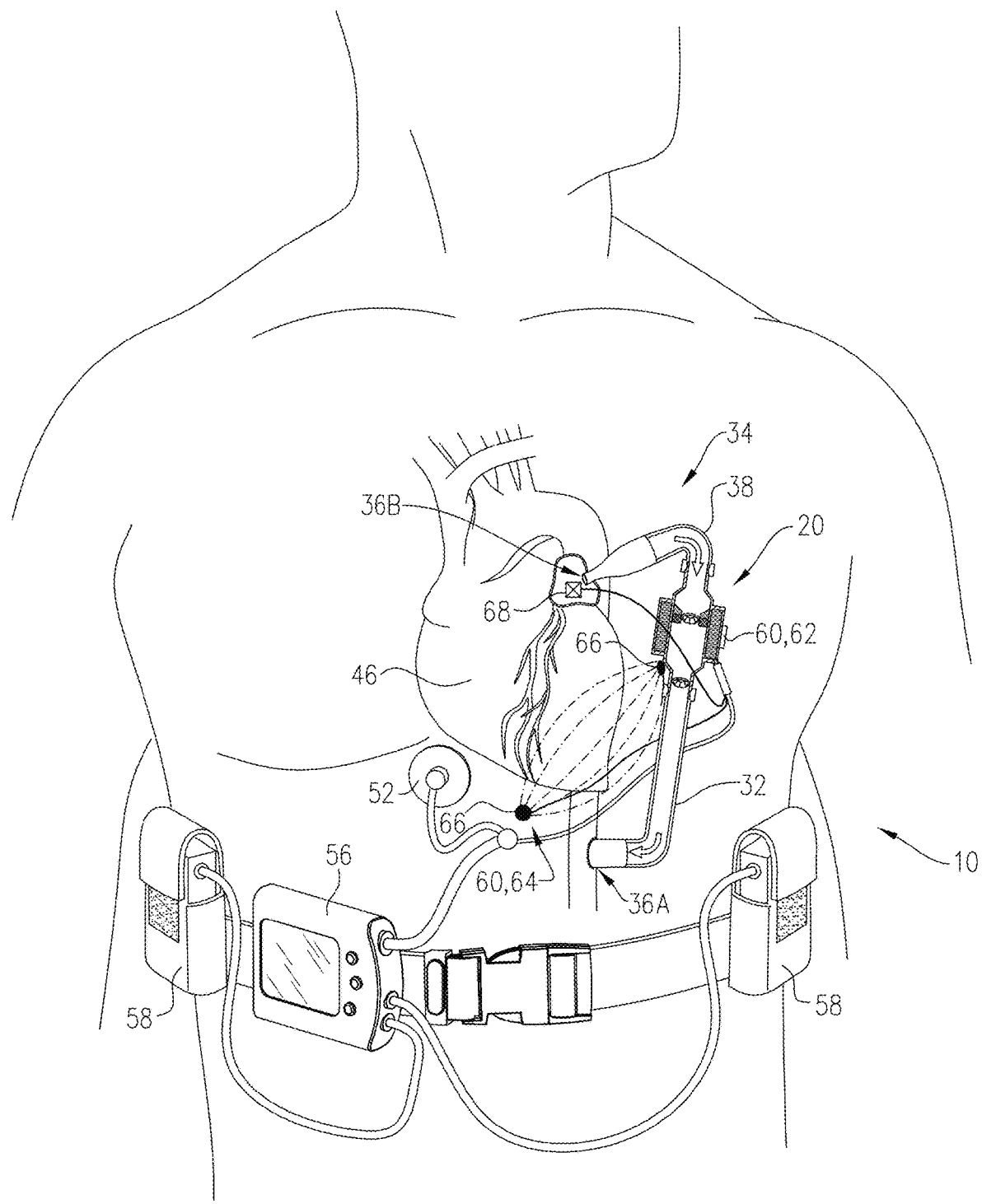
FIG. 1 is a schematic cross-sectional illustration of a left ventricular assist device (LVAD) system applied to a patient, in accordance with an application of the present invention.

FIG. 1 is a schematic cross-sectional illustration of a left ventricular assist device (LVAD) system 10 applied to a patient, in accordance with an application of the present invention.

Figure 2:
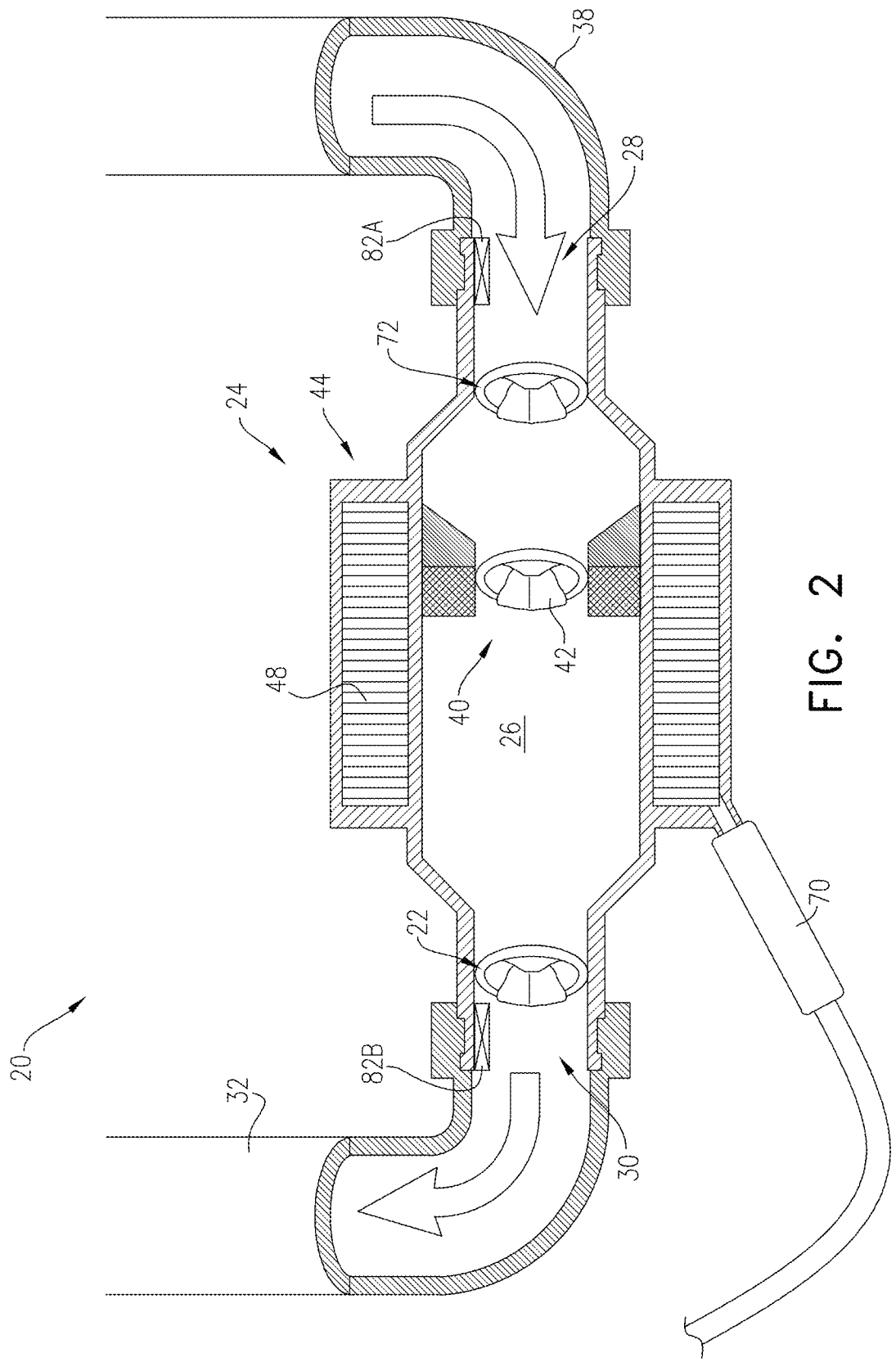
FIG. 2 is a schematic illustration of an implantable LVAD of the LVAD system of FIG. 1, in accordance with an application of the present invention.

FIG. 2 is a schematic illustration of an implantable LVAD 20 of LVAD system 10, in accordance with an application of the present invention.

LVAD 20 comprises:

a stationary one-way outflow valve 22;

a pump 24, which (a) is shaped so as to define a pump chamber 26 having an upstream inflow end 28 and a downstream outflow end 30;

an outflow cannula 32, which is (a) couplable in fluid communication with a circulatory system 34 of the patient at a first site 36A, and (b) arranged in fluid communication with downstream outflow end 30 of pump chamber 26 via stationary one-way outflow valve 22; stationary one-way outflow valve 22 is configured to allow downstream blood flow from pump chamber 26 to outflow cannula 32 and to inhibit upstream blood flow from outflow cannula 32 to pump chamber 26; and an inflow cannula 38, which is (a) couplable in fluid communication with circulatory system 34 at a second site 36B upstream of first site 36A, and (b) arranged to allow downstream blood flow from inflow cannula 38 to upstream inflow end 28 of pump chamber 26 (e.g., is arranged in fluid communication with upstream inflow end 28 of pump chamber 26).

Pump 24 is a positive displacement (PD) pump, and typically comprises a tubular 44, which comprises:

a magnetic piston 40, which comprises a reciprocating one-way valve 42 configured to allow downstream blood flow and inhibit upstream blood flow; and a stator 48, which is configured to magnetically drive magnetic piston 40 with reciprocating motion (such that magnetic piston 40 serves as the slider of tubular linear motor 44), so as to pump blood downstream during downstream motion of magnetic piston 40 while reciprocating one-way valve 42 is closed.

Stator 48 comprises coil windings, as is known in the tubular linear motor art. Tubular linear motor 44 is typically configured a levitating linear motor, in the sense that magnetic piston 40 slides within stator 48 without bearings, i.e., tubular linear motor 44 is bearingless.

LVAD 20 typically generates laminar blood flow without turbulence, which results in low shear stress on red blood cells, thereby reducing the likelihood of hemolysis and thrombosis.

LVAD system 10 typically further comprises:
- a cardiac sensor 52, configured to sense one or more features of a plurality of cardiac cycles of a heart 46;
- control circuitry 56, which is coupled to cardiac sensor 52 and configured to activate tubular linear motor 44 to provide pulsatile flow synchronized with the cardiac cycles; and
- typically, a power source 58 (e.g., comprising one or more batteries) arranged to provide power to tubular linear motor 44.

Typically, cardiac sensor 52 comprises one or more implantable or external ECG electrodes, which are configured to sense components of an ECG of the patient. Other components of cardiac sensor 52, such as electronics, may be located either within LVAD 20 or in an external component of LVAD system 10, such as circuitry 56.

For some applications, at least a portion of control circuitry 56 and/or power source 58 are configured to be placed outside the patient's body. For these applications, LVAD system 10 may further comprise a percutaneous lead 70, which couples control circuitry 56 to LVAD 20 and/or power source 58. For example, percutaneous lead 70 may have a small diameter, e.g., 2 mm, which may reduce the risk of infection. Alternatively, control circuitry 56 and/or power source 58 may be wirelessly coupled to LVAD 20.

For some applications, at least a portion of an internal surface of pump chamber 26 is coated with a diamond-like carbon (DLC) coating.

Typically, the blood-contacting surfaces of LVAD 20 comprise bioprosthetic materials.

In an application of the present invention, LVAD system 10 comprises one or more activity sensors 60, which are configured to sense a level of activity of the patient. For example, the one or more activity sensors 60 may comprise one or more of the following sensors:
- an accelerometer 62, which is configured to sense the level of activity of the patient by sensing motion of the patient, and/or
- a respiration sensor 64, which is configured to sense the level of activity of the patient by sensing one or more parameters of respiration of the patient; for example, respiration sensor 64 may measure changes in respiration rate and/or lung volume based on transthoracic impedance, and, to this end, may comprise at least two electrodes 66 (which are typically implantable) between which impedance of one or both lungs is measured.

In an application of the present invention, control circuitry 56 is configured to adapt the stroke volume provided by tubular linear motor 44 according the metabolic demands, as indicated by the level of activity of the patient sensed using the one or more activity sensors 60. This may mimic to some extent the healthy heart, in which the stroke volume varies according to metabolic demands (in accordance with the Frank-Starling law).

In some applications of the present invention, control circuitry 56 is configured to activate tubular linear motor 44 to provide pulsatile flow synchronized with the cardiac cycles by, during each of the cardiac cycles:
- activating stator 48, during a first portion of the cardiac cycle, to move the magnetic piston downstream during a first period of time, and
- activating stator 48, during a second portion of the cardiac cycle, to move the magnetic piston upstream during a second period of time.

The first portion of the cardiac cycle is at least a portion of one of systole or diastole, and the second portion of the cardiac cycle is at least a portion of the other of systole or diastole.

As used in the present application, including in the claims, systole refers to ventricular systole, and diastole refers to ventricular diastole.

In an application of the present invention, control circuitry 56 is configured to activate tubular linear motor 44 to provide pulsatile flow synchronized with the cardiac cycles by:
- during at least a portion of systole of each of the cardiac cycles, activating stator 48 to move magnetic piston 40 downstream at a velocity set based on a target stroke volume and a target stroke duration, and
- during at least a portion of diastole of each of the cardiac cycles, activating stator 48 to move magnetic piston 40 upstream.

Thus, control circuitry 56 uses the target stroke volume and target stroke duration as inputs to calculate (e.g., mathematically or using a lookup table) the velocity of magnetic piston 40, such that magnetic piston 40 moves during the entirety of the target stroke duration, rather than moving the magnetic piston at a predetermined rate for the amount of time necessary to provide the target stroke volume. Utilizing the entire available target stroke duration may reduce peak energy consumption and/or provide pumping that more closely mimics the natural physiological pumping.

Typically, LVAD 20 is configurable to provide a stroke volume of 1-90 cc per cardiac cycle. LVAD 20 controls the provided stroke volume by setting a distance that magnetic piston 40 moves during pumping during each cardiac cycle. Typically, LVAD 20 is configured to set the stroke volume to less than a healthy heart's natural stroke volume (e.g., less than 80%-90% of a healthy heart's natural stroke volume).

For some applications, control circuitry 56 is configured to allow the target stroke volume to be manually programmed by a physician.

For some applications, control circuitry 56 is configured to set the target stroke volume responsively to the level of activity of the patient sensed using one or more activity sensors 60.

For some applications, control circuitry 56 is configured to set the target stroke duration responsively to the sensed one or more features of the plurality of cardiac cycles, such as responsively to a duration of systole of the plurality of cardiac cycles, e.g., equal to a fraction of the duration of systole of the plurality of cardiac cycles.

For some applications, LVAD system 10 further comprises a left atrial pressure sensor 68, which is configured to sense left atrial pressure. Control circuitry 56 is configured to set the target stroke volume at a level that prevents the sensed left atrial pressure from exceeding a threshold pressure. For example, the threshold pressure may be 12-15 mmHg.

Reference is again made to FIG. 2. For some applications, LVAD system 10 further comprises an upstream pressure sensor 82A and/or a downstream pressure sensor 82B, which are configured to measure blood pressure of blood entering upstream inflow end 28 of pump chamber 26 and blood exiting downstream outflow end 30 of pump chamber 26, respectively. For some applications, LVAD system 10 is configured to:

- detect a malfunction and/or blockage of pump 24 based on a difference between the pressures sensed by upstream and downstream pressure sensors 82A and 82B, in which case LVAD system 10 typically ceases pumping and generates an alert to the patient and/or a healthcare provider,
- reduce the stroke volume if the pressure sensed by downstream pressure sensor 82B exceeds a threshold value (e.g., 120 mmHg), which may be harmful for the patient, and/or
- reduce the stroke volume if the pressure sensed by upstream pressure sensor 82A falls below a threshold value, because insufficient inflow blood is available to provide the desired stroke volume.

Alternatively or additionally, LVAD system 10 may further comprise a flow sensor, which is configured to measure a velocity and/or volume of blood flow through pump 24.

For some applications, LVAD system 10 is configured to reduce the stroke volume if the current consumed by the tubular linear motor 44 exceeds a threshold value (typically measured in mA); the threshold value typically varies based on the stroke volume (e.g., based on a graph). The stroke volume is typically reduced until the current consumption falls below the threshold value for the reduced stroke volume. This feature may prevent tubular linear motor 44 from consuming more current than can or should be provided by the one or more batteries of the system.

Reference is made to FIG. 2. For some applications, implantable LVAD 20 further comprises a stationary one-way inflow valve 72. Inflow cannula 38 is arranged to allow the downstream blood flow from inflow cannula 38 to upstream inflow end 28 of pump chamber 26 via stationary one-way inflow valve 72 (e.g., is arranged in fluid communication with upstream inflow end 28 of pump chamber 26 via stationary one-way inflow valve 72). Stationary one-way inflow valve 72 is configured to allow downstream blood flow from inflow cannula 38 to pump chamber 26 and to inhibit upstream blood flow from pump chamber 26 to inflow cannula 38. Stationary one-way inflow valve 72 may prevent upstream propagation of any shock waves that may be generated by upstream motion of magnetic piston 40. Alternatively, as shown in the other figures, implantable LVAD 20 does not comprise stationary one-way inflow valve 72.

Figure 3A:
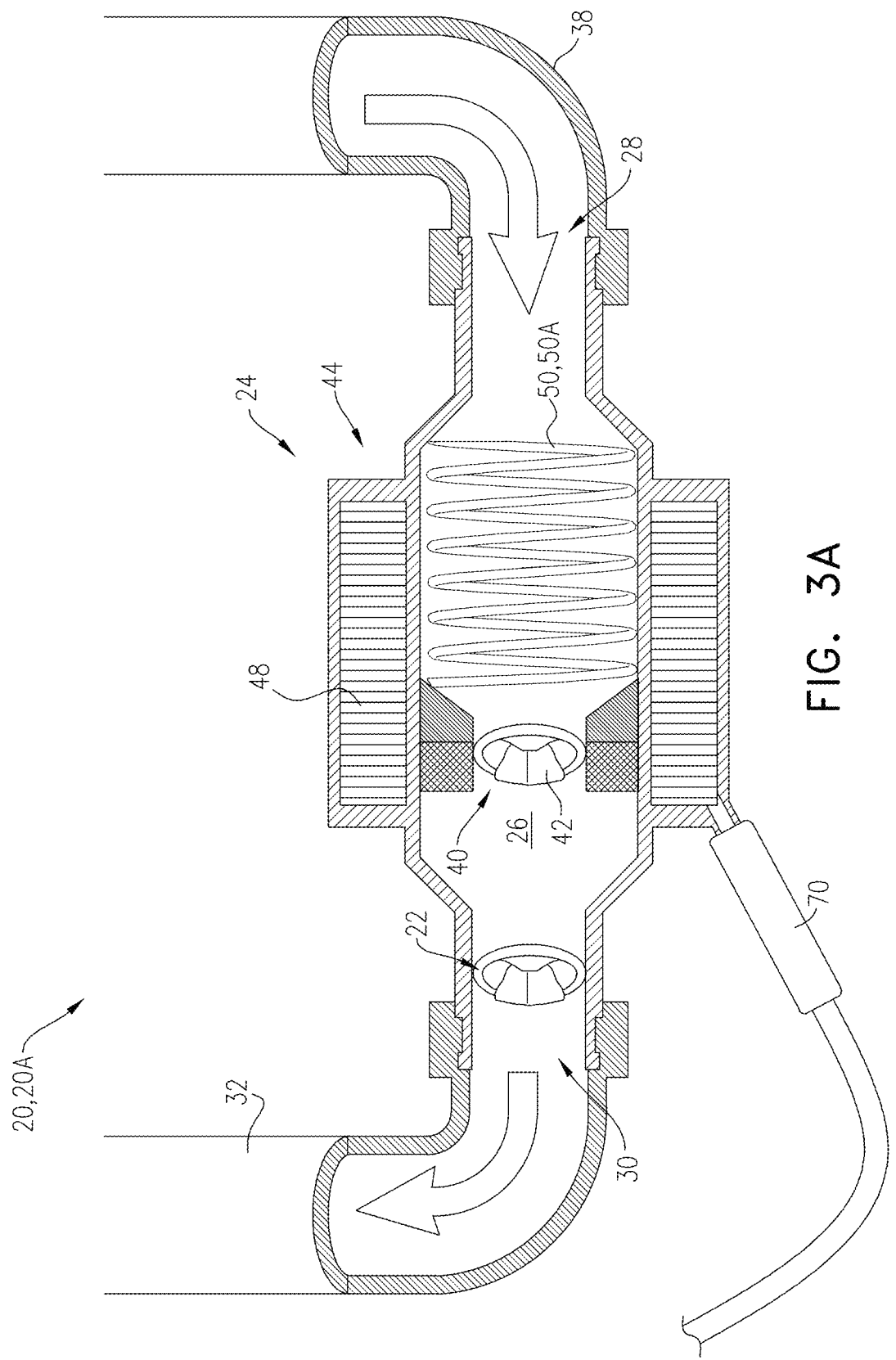
FIGS. 3A-B are schematic cross-sectional illustrations of alternative configurations of the implantable LVAD of FIG. 2, in accordance with respective applications of the present invention.
Figure 3B:
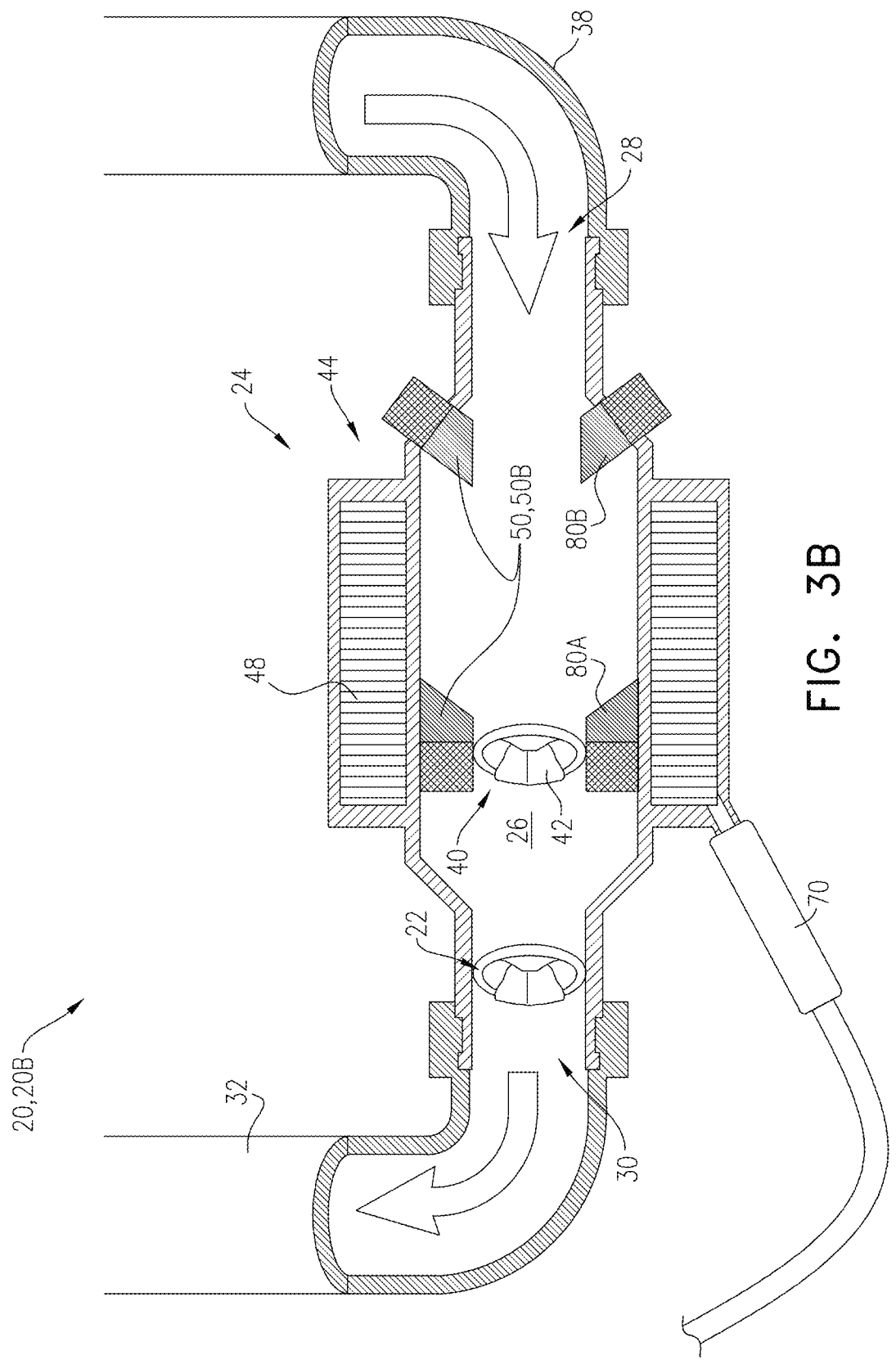

Reference is now made to FIGS. 3A-B, which are schematic cross-sectional illustrations of alternative configurations of implantable LVAD 20, in accordance with respective applications of the present invention.

In these configurations of LVAD 20, pump 24 further comprises a spring 50, which is arranged to store energy during upstream motion of magnetic piston 40 and release the stored energy during the downstream motion of magnetic piston 40. Control circuitry 56 is configured to activate tubular linear motor 44 to provide pulsatile flow synchronized with the cardiac cycles by, during each of the cardiac cycles:

- activating stator 48, during at least a portion of systole, to move magnetic piston 40 downstream during a first period of time having a first duration, and
- activating stator 48, during at least a portion of diastole, to move magnetic piston 40 upstream during a second period of time having a second duration.

The motion of magnetic piston 40 upstream during the second period stores energy in spring 50. Spring 50 releases the stored energy during systole, thereby reducing the amount of energy that tubular linear motor 44 must apply during systole in order to achieve a given amount of downstream motion of magnetic piston 40. This allocation of activation of tubular linear motor 44 between diastole and systole reduces the peak power consumed by tubular linear motor 44 during systole, which may reduce the motor's demands on power source 58 (which, as mentioned above, may comprise one or more batteries). For example, control circuitry 56 and spring 50 may be configured such that, during each of the cardiac cycles, peak power consumed by tubular linear motor 44 during systole is no more than three times, such as no more than two times, peak power consumed by tubular linear motor 44 during diastole.

For some applications, the second duration is greater than the first duration.

For some applications, such as shown in FIG. 3A, LVAD 20 comprises an implantable LVAD 20A, and spring 50 comprises an elastic spring 50A. For example, spring 50A may comprise a compression spring (as shown) or an extension spring (configuration not shown), or any other type of spring known in the mechanical arts. Spring 50A is coupled between magnetic piston 40 and a location fixed with respect to pump chamber 26.

For other applications, such as shown in FIG. 3B, LVAD 20 comprises an implantable LVAD 20B, and spring 50 comprises a magnetic spring 50B, which comprises a first moveable magnet 80A and a second stationary magnet 80B. Magnetic piston 40 comprises first moveable magnet 80A. First moveable magnet 80A may be one of the magnets of magnetic piston 40 used for the motorized motion of the magnetic piston, such as shown, or may be a separate magnet coupled to magnetic piston 40. Second stationary magnet 80B is coupled to pump 24 at a fixed location with respect to pump chamber 26, such as at a location axially upstream of magnetic piston 40, e.g., axially between magnetic piston 40 and upstream inflow end 28 of pump chamber 26. For example, the respective magnetic poles of first and second magnets 80A and 80B may be oriented in opposite directions, such that poles having the same polarity face each other.

Figure 4:
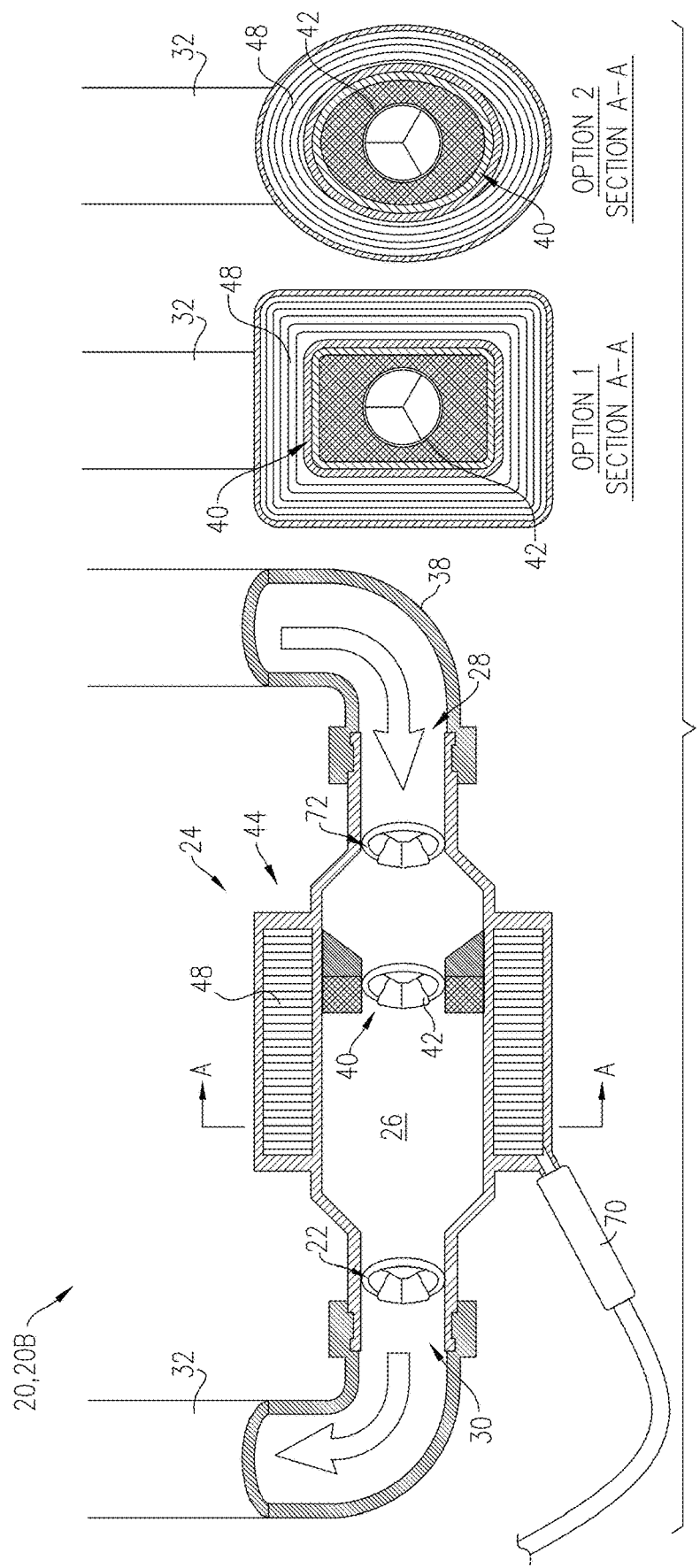
FIG. 4 is a schematic illustration of yet additional configurations of the implantable LVAD of FIG. 2, in accordance with respective applications of the present invention.

Reference is now made to FIG. 4, which is a schematic illustration of yet additional configurations of implantable LVAD 20, in accordance with respective applications of the present invention. The features of these configurations may be implemented in combination with the features of any of the other configurations of implantable LVAD 20 described herein, mutatis mutandis, and like reference numerals refer to like parts.

In these configurations, an inner surface of pump chamber 26 and an outer surface of magnetic piston 40 of pump 24 have respective elongate non-circular cross-sections perpendicular to a central longitudinal axis of pump chamber 26, each of which cross-sections has a greatest dimension in one direction that is greater than a greatest dimension in a perpendicular direction. For example, the elongate non-circular cross-sections may be rectangular or elliptical, as shown. The elongate cross-sections provide a lower profile than a circular configuration, which may facilitate subcutaneous implantation. For example, rectangular cross-sections may provide a more accurate mechanism than an elliptical cross-sectional shape, because the outer surface of magnetic piston 40 may experience less friction with the inner surface of pump chamber 26 and be less likely to jam.

Figure 5A:
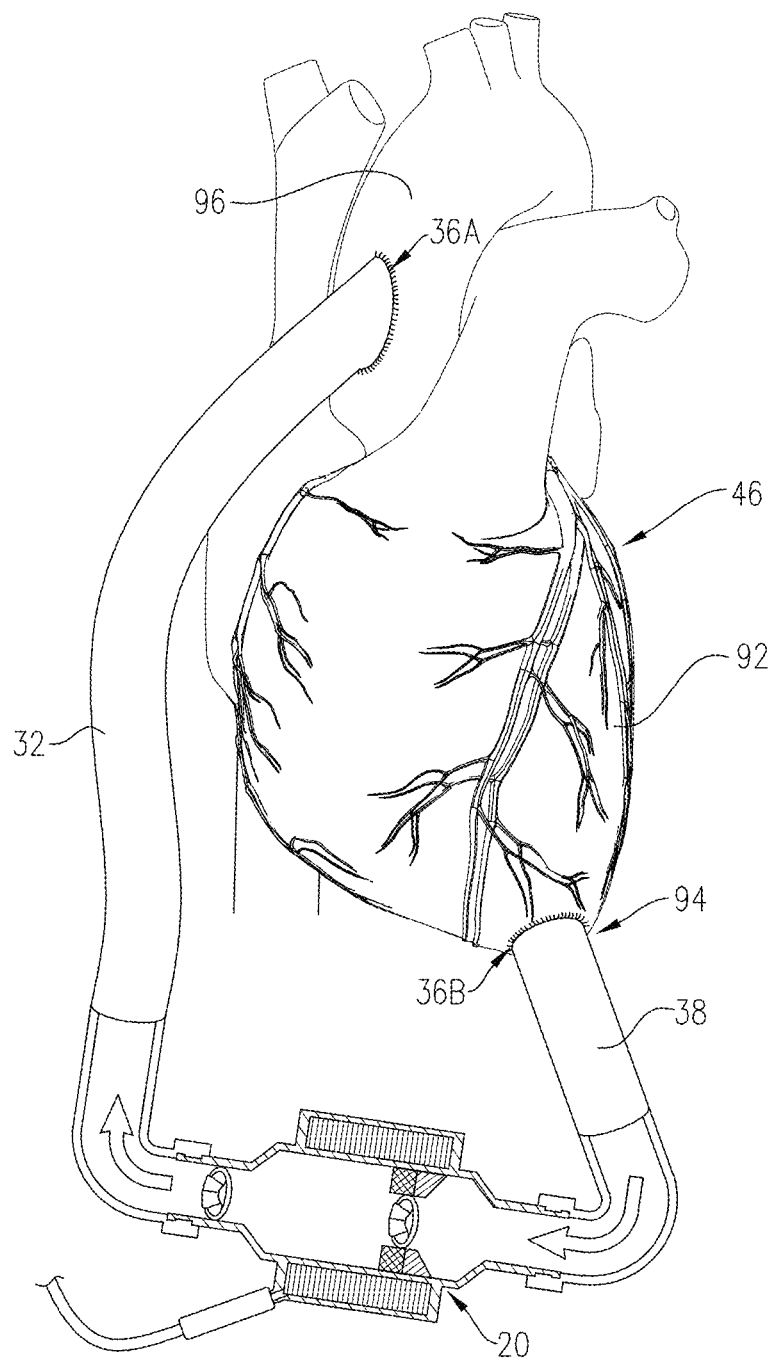
Figure 5B:
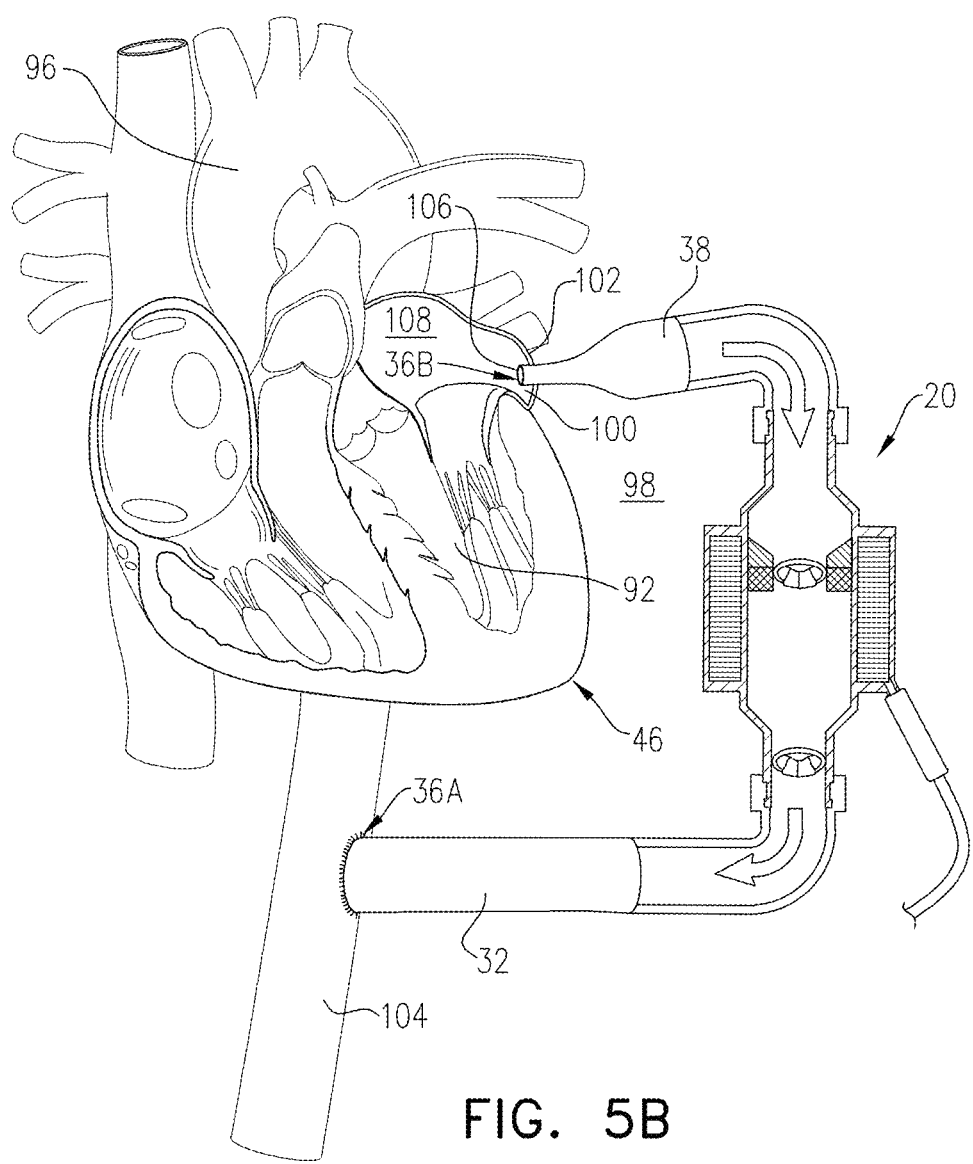
Figure 5C:
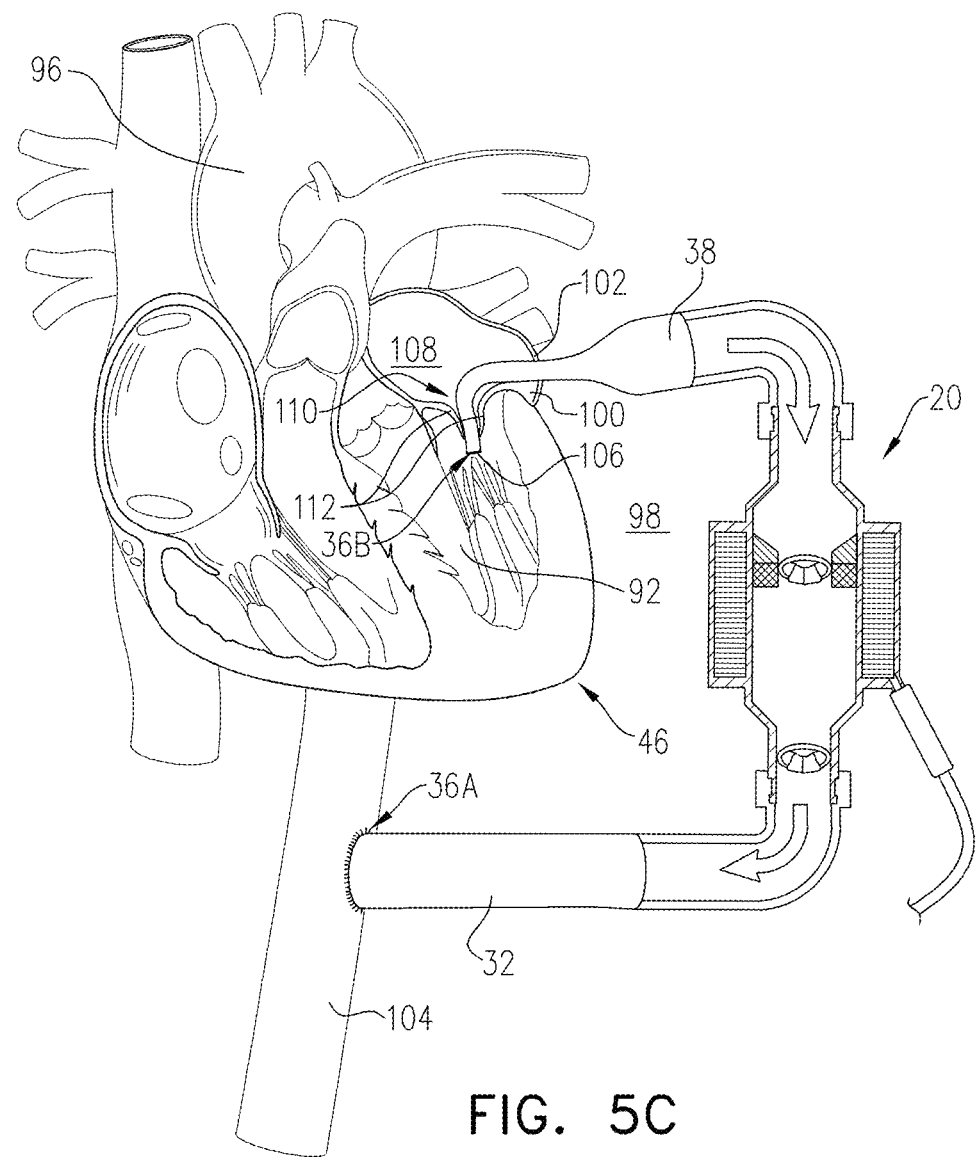

Reference is now made to FIGS. 5A-C, which are schematic illustrations of methods of coupling an implantable LVAD in fluid communication with circulatory system 34.

FIG. 5A shows a conventional coupling technique, in which inflow cannula 38 is inserted into a left ventricle 92 at the left ventricle's apex 94, and outflow cannula 32 is coupled to an ascending aorta 96 at first site 36A. In this conventional technique, a thoracic cavity 98 of the patient is accessed, typically by performing a sternotomy, which is commonly used for implanting LVADs, in order to provide access to both the left ventricle's apex 94 and ascending aorta 96.

FIGS. 5B and 5C show additional coupling techniques, in accordance with respective applications of the present invention. In these techniques, thoracic cavity 98 of the patient is accessed, typically by performing a left thoracotomy. As is known in the general surgical arts, a left thoracotomy is generally less traumatic than the sternotomy commonly used in conventional LVAD implantation techniques.

After accessing thoracic cavity 98, an LVAD (either LVAD 20 or an LVAD known in the art) is transthoracically implanted in the patient by:
  transmurally inserting an inflow cannula of the LVAD into a left atrial appendage (LAA) 100 of heart 46, and securing the inflow cannula to a left atrial wall 102 (such as by stitching around the inflow cannula on an external surface of left atrial wall 102), and
  anastomosing an outflow cannula of the LVAD to a descending aorta 104 at first site 36A.

Generally, it is easier to attach the outflow cannula to descending aorta 104 than ascending aorta 96, because of the easier access available to the descending aorta than to the ascending aorta.

In the technique shown in FIG. 5B, an inflow end opening 106 of the inflow cannula is positioned in a left atrium 108 (either in LAA 100 or outside LAA 100). Securing the inflow cannula to left atrial wall 102 holds inflow end opening 106 of the inflow cannula in left atrium 108.

In the technique shown in FIG. 5C, inserting the inflow cannula into LAA 100 comprises passing inflow end opening 106 of the inflow cannula through a mitral valve 110 into left ventricle 92. Securing the inflow cannula to left atrial wall 102 holds inflow end opening 106 of the inflow cannula in left ventricle 92.

For some applications, in the technique shown in FIG. 5C, implanting the LVAD comprises identifying that the patient suffers from mitral regurgitation, and passing inflow end opening 106 of the inflow cannula through mitral valve 110 into left ventricle 92 causes leaflets 112 of the mitral valve to at least partially contact an outer surface of the inflow cannula during systole, thereby reducing mitral regurgitation.

FIG. 5D shows another coupling technique, in which the inflow cannula is inserted into left ventricle 92, such as via mitral valve 110, for example by one of the following approaches:
  transeptally via a right atrium 114 and an inferior vena cava 116 (e.g., using a transfemoral venous approach), such as shown,
  via LAA 100, such as described hereinabove with reference to FIG. 5C, or
  through the left ventricle's apex 94, such as described hereinabove with reference to FIG. 5A.

Alternatively, the inflow cannula is inserted into left atrium 108 via LAA 100, such as described hereinabove with reference to FIG. 5B.

For some applications, such as shown in FIG. 5D, the outflow cannula is coupled to a left subclavian artery 118 at first site 36A, typically by anastomosis. Alternatively, for some applications, the outflow cannula is coupled to descending aorta 104 at first site 36A, typically by anastomosis, such as described hereinabove with reference to FIG. 5C.

Alternatively, for some applications (configurations not shown), the outflow cannula is coupled to ascending aorta 96, typically by anastomosis, and/or the inflow cannula is inserted into left ventricle 92 through a wall of ascending aorta 96 and an aortic valve.

Reference is made to FIGS. 1-5D. In some applications of the present invention, LVAD system 10 is configured to operate in a counterpulsation mode, in which pump 24 is activated to pump blood downstream during diastole, rather than during systole in the normal operating mode described hereinabove. For example, in the configuration described hereinabove with reference to FIGS. 3A-B, control circuitry 56 is configured to activate tubular linear motor 44 to provide pulsatile flow synchronized with the cardiac cycles by, during each of the cardiac cycles: (a) activating stator 48, during at least a portion of diastole, to move magnetic piston 40 downstream during a first period of time having a first duration, and (b) activating stator 48, during at least a portion of systole, to move magnetic piston 40 upstream during a second period of time having a second duration. For some applications, the second duration is less than the first duration. The other techniques of this configuration described above may optionally be implemented, by swapping systole and diastole.

Figure 6A:
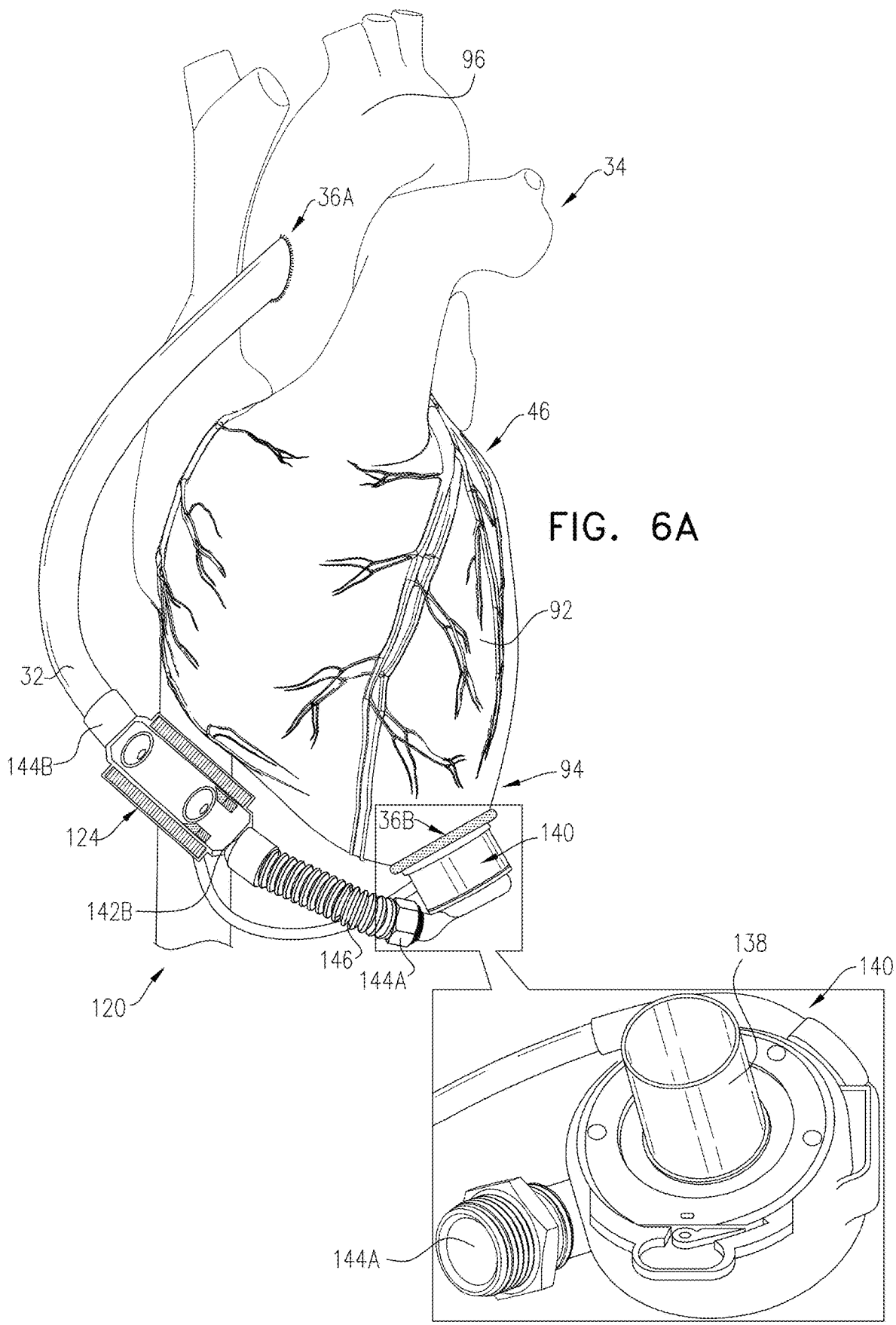
FIGS. 6A-B are schematic illustrations of another LVAD applied to a patient, in accordance with an application of the present invention.
Figure 6B:
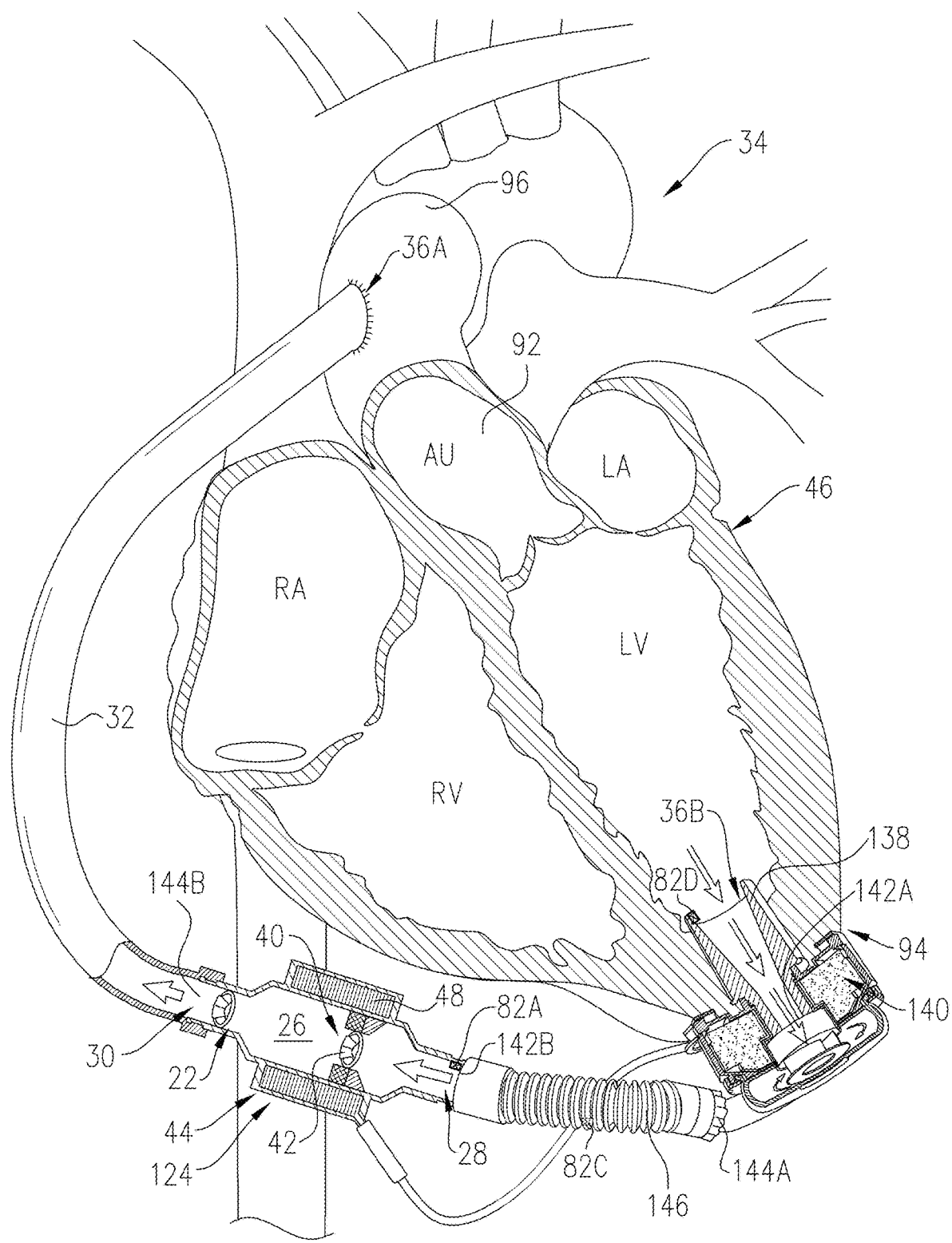

Reference is now made to FIGS. 6A-B, which are schematic illustrations of a left ventricular assist device (LVAD) 120 applied to a patient, in accordance with an application of the present invention. LVAD 120 is typically a component of an LVAD system, such as LVAD system 10, described hereinabove with reference to reference to FIG. 1. The LVAD system comprising LVAD 120 may implement any the features of LVAD system 10 described hereinabove, mutatis mutandis, and LVAD 120 may implement any of the features of LVAD 20 described hereinabove, mutatis mutandis; for example, LVAD 120 may or may not comprise spring 50, and the control circuitry may or may not be configured to activate stator 48 to move magnetic piston 40 downstream at a velocity set based on a target stroke volume and a target stroke duration, during at least a portion of systole of each of the cardiac cycles.

LVAD 120 comprises:
  outflow cannula 32, which is couplable in fluid communication with circulatory system 34 of the patient at first site 36A;
  an inflow cannula 138, which is couplable in fluid communication with circulatory system 34 at a second site 36B upstream of first site 36A;
  a continuous-flow pump 140, which comprises (1) a first inlet 142A in fluid communication with inflow cannula 138, and (2) a first outlet 144A; and
  a pulsatile-flow pump 124, which comprises (1) a second inlet 142B and (2) a second outlet 144B, which is in fluid communication with outflow cannula 32.

Second inlet 142B of pulsatile-flow pump 124 is in fluid communication with first outlet 144A of continuous-flow pump 140, and thus with inflow cannula 138 via continuous-flow pump 140. Inflow cannula 138 is therefore arranged to allow downstream blood flow from inflow cannula 138 to second inlet 142B. Pulsatile-flow pump 124 may implement any of the features of pump 24, described hereinabove, mutatis mutandis, or may comprise a different kind of pulsatile-flow positive displacement pump known in the art.

The LVAD system comprising LVAD 120 further comprises control circuitry, which may implement any of the features of control circuitry 56, described hereinabove, mutatis mutandis. (The control circuitry is not shown in FIGS. 6A-B, but may be similar to circuitry 56 shown in FIG. 1 for LVAD system 10.) The control circuitry is typically configured to:
- activate continuous-flow pump 140 to provide flow without synchronization with cardiac cycles of a heart of the patient, and
- activate pulsatile-flow pump 124 to provide pulsatile flow synchronized with the cardiac cycles.

Alternatively, the control circuitry is configured to activate pulsatile-flow pump 124 to provide the pulsatile flow without synchronization with the cardiac cycles of the heart, such as at a constant or adjustable pulsation rate, e.g., 1 pulse per minute. This mode of operation may be appropriate, for example, for a very weak heart.

For some applications, the LVAD system comprising LVAD 120 further comprises cardiac sensor 52, which is configured to sense one or more features of the cardiac cycles, such as described hereinabove. The control circuitry is coupled to cardiac sensor 52.

For some applications, the control circuitry is configured to activate pulsatile-flow pump 124 to provide pulsatile flow synchronized with the cardiac cycles by, during each of the cardiac cycles, activating pulsatile-flow pump 124 to pump blood downstream during a portion of systole of the cardiac cycle, and not to pump blood downstream during any portion of diastole of the cardiac cycle, such as described hereinabove regarding control circuitry 56.

For some applications, the LVAD system comprising LVAD 120 further comprises stationary one-way outflow valve 22, which is arranged to allow downstream blood flow from second outlet 144B of pulsatile-flow pump 124 to outflow cannula 32, and to inhibit upstream blood flow from outflow cannula 32 to second outlet 144B.

For some applications, the LVAD system comprising LVAD 120 further comprises a tube 146 which couples second inlet 142B of pulsatile-flow pump 124 in the fluid communication with first outlet 144A of continuous-flow pump 140.

For some applications, pulsatile-flow pump 124:
- is shaped so as to define pump chamber 26 having (a) upstream inflow end 28 in fluid communication with second inlet 142B, and (b) downstream outflow end 30 in fluid communication with second outlet 144B, and
- comprises tubular linear motor 44, which comprises (a) magnetic piston 40, which comprises reciprocating one-way valve 42 configured to allow downstream blood flow and inhibit upstream blood flow; and (b) stator 48, which is configured to magnetically drive magnetic piston 40 with reciprocating motion, so as to pump blood downstream during downstream motion of magnetic piston 40 while reciprocating one-way valve 42 is closed.

For some of these applications, the control circuitry is configured to activate tubular linear motor 44 to provide the pulsatile flow synchronized with the cardiac cycles by, during each of the cardiac cycles:
- activating stator 48 of tubular linear motor 44 to move magnetic piston 40 downstream during a portion of systole of the cardiac cycle, and
- activating stator 48 of tubular linear motor 44 to move magnetic piston 40 upstream during a portion of diastole of the cardiac cycle.

For some applications, such as shown in FIG. 4 for LVAD system 10, the LVAD system comprising LVAD 120 further comprises stationary one-way inflow valve 72, which is arranged to allow downstream blood flow into pump chamber 26 of pulsatile-flow pump 124, and to inhibit upstream blood flow from pump chamber 26.

Continuous-flow pump 140 may comprise any type of continuous-flow pump known in the LVAD art. For example, continuous-flow pump 140 may comprise a magnetically-levitated centrifugal pump. Optionally, continuous-flow pump 140 comprises all or a portion of a commercially-available continuous-flow LVAD, such as, for example, the HeartMate 3 LVAD (St. Jude Medical, St. Paul, MN, USA), or HeartWare™ HVAD™ (Medtronic, Minneapolis, MN, USA).

For some applications, first site 36A is one of the first sites 36A described hereinabove with reference to FIGS. 1 and/or FIGS. 1A-D.

For some applications, second site 36B is apex 94 of left ventricle 92 of heart 46, such as shown in FIGS. 6A-B, or one of the second sites 36B shown in FIG. 1, 5B, or 5C.

Figure 7:
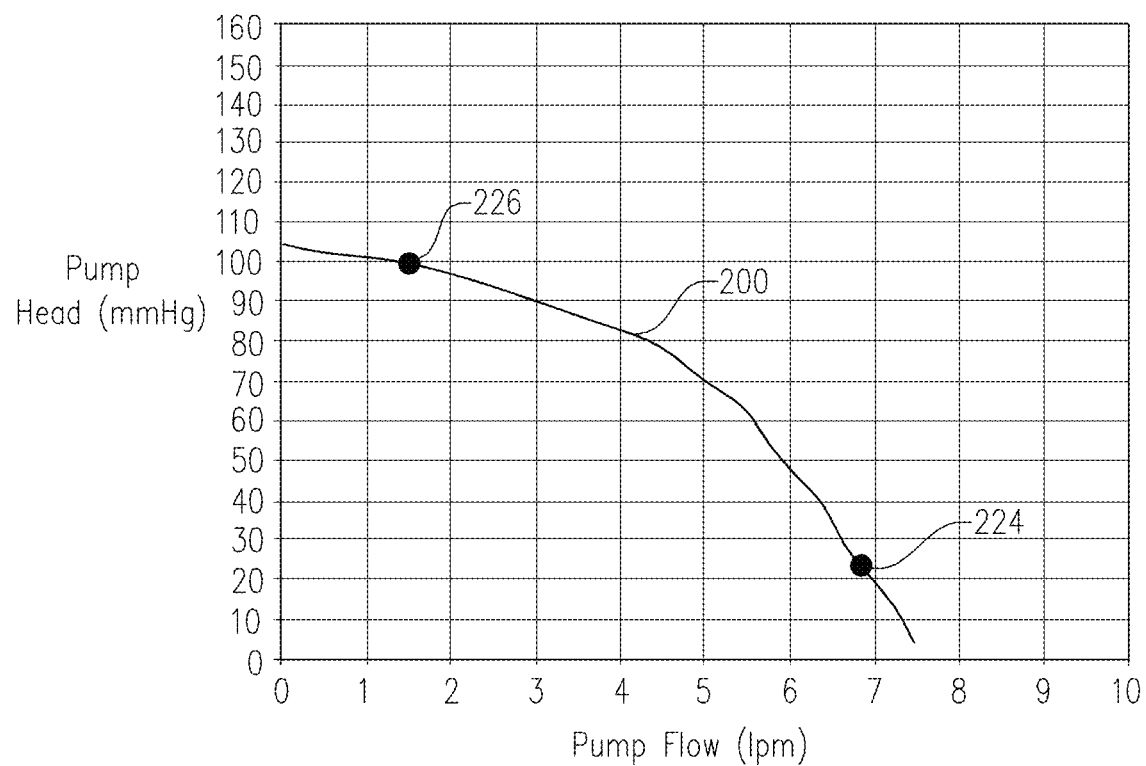
FIG. 7 is an illustrative pump curve for a continuous-flow magnetically a levitated centrifugal pump of conventional LVAD, as known in the prior art.

Reference is now made to FIG. 7, which is an illustrative pump curve 200 for a continuous-flow magnetically levitated centrifugal pump of a conventional LVAD, as known in the prior art. By way of example, pump curve 200 may be representative of a pump speed of 5,500 rpm. As indicated by pump curve 200, the higher the pump head (delta pressure across pump), the lower the pump flow.

Figure 8A:
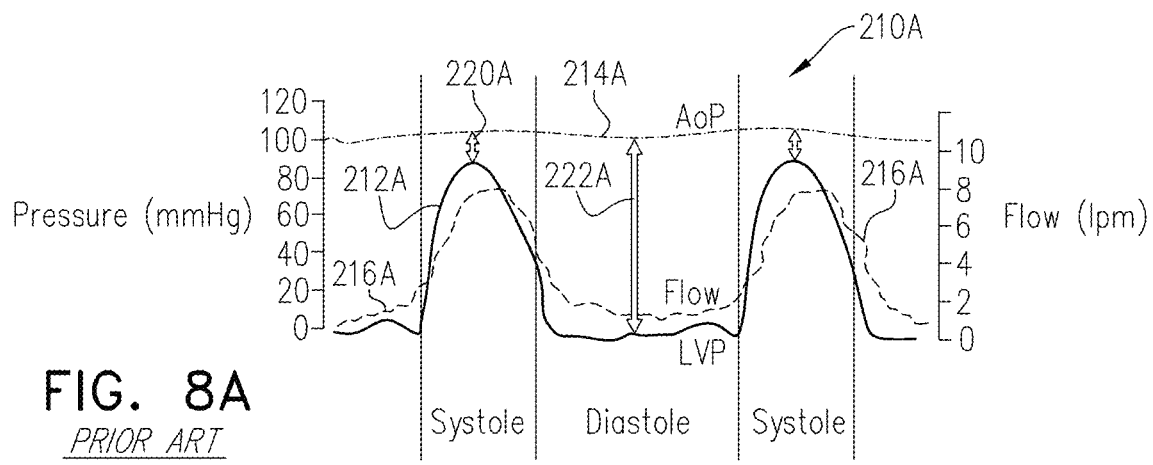
FIG. 8A is an illustrative graph showing blood pressure and blood flow rate for a continuous-flow magnetically levitated centrifugal pump of a conventional LVAD, as known in the prior art.

Reference is further made to FIG. 8A, which is an illustrative graph 210A showing blood pressure and blood flow rate for a continuous-flow magnetically levitated centrifugal pump of a conventional LVAD, as known in the prior art. Graph 210A includes:
- a left-ventricular-pressure (LVP) curve 212A, measured in mmHg,
- an aortic pressure (AoP) curve 214A, also measured in mmHg, and
- a flow rate curve 216A, indicative of blood flow through the LVAD pump, measured in liters per minutes (lpm).

In a continuous-flow LVAD pump, for any given pump speed, the flow rate is driven largely by the delta pressure across the pump, i.e., the difference between AoP and LVP, as indicated by pump curve 200 of FIG. 7. As a result:
- during systole, as LVP increases substantially, while AoP increases only slightly, the delta pressure is small, resulting in high flow, as indicated by a systolic delta arrow 220A in FIG. 8A and a systolic point 224 in FIG. 7; and
- during diastole, as LVP decreases substantially, while AoP decreases only slightly, the delta pressure is large, resulting in low flow, as indicated by a diastolic delta arrow 222A in FIG. 8A a diastolic point 226 in FIG. 7.

As can be seen in AOP curve 214A, although conventional continuous-flow LVAD pumps produce some aortic pulsatility, the pulsatility is minimal. Because of this low pulsatility, continuous-flow LVADs are associated with altered arterial baroreceptors, because reduced pulsatility leads to increased sympathetic activation and peripheral vascular resistance.

Figure 8B:
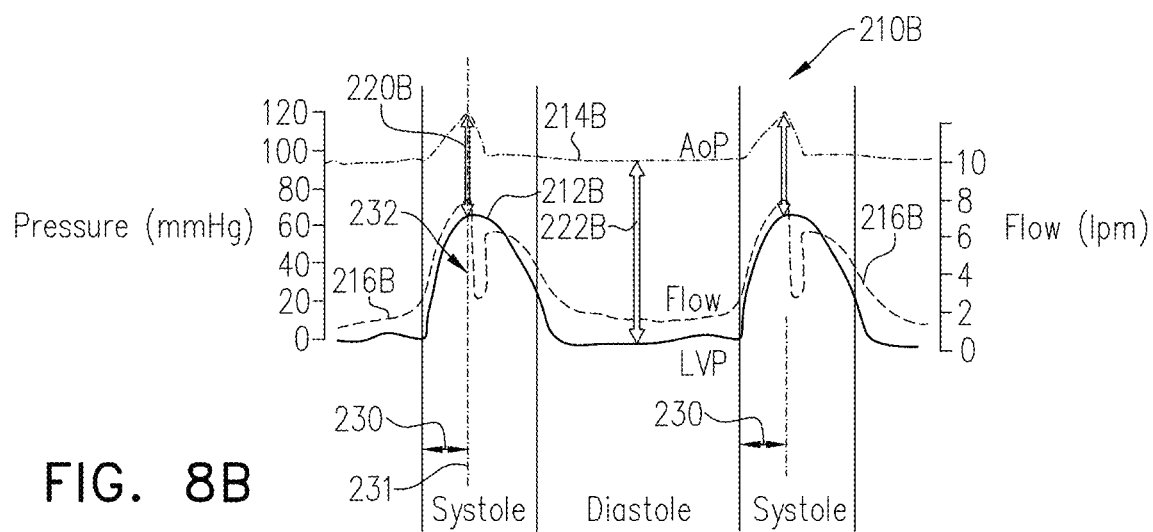
FIGS. 8B and 8C are illustrative graphs showing blood pressure and blood flow rate for the LVAD of FIGS. 6A-B, in accordance with respective applications of the present invention.
Figure 8C:
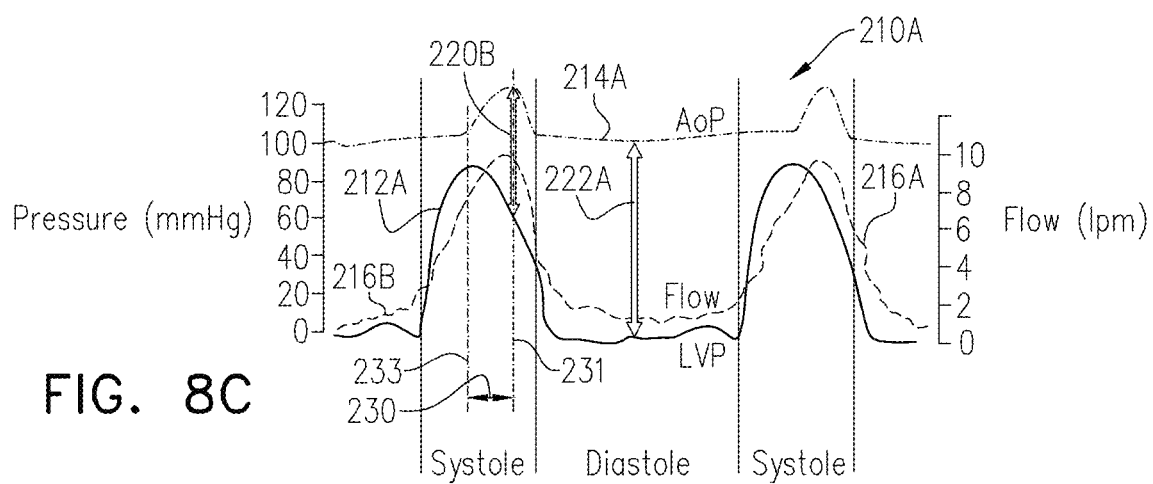

Reference is now made to FIGS. 8B and 8C, which are illustrative graphs 210B showing blood pressure and blood flow rate for LVAD 120, in accordance with respective applications of the present invention. Graphs 210B include:
- a left-ventricular-pressure (LVP) curve 212B, measured in mmHg,
- an aortic pressure (AoP) curve 214B, also measured in mmHg, and
- a flow rate curve 216B, indicative of blood flow through LVAD 120 (through both continuous-flow pump 140 and pulsatile-flow pump 124, in series), measured in liters per minute (lpm).

Graphs 210B reflect the combined effect of pulsatile-flow pump 124 and continuous-flow pump 140, as follows.

During a portion 230 of systole in which pulsatile-flow pump 124 pumps blood (as magnetic piston 40 moves downstream), blood flow through LVAD 120, as reflected by flow rate curve 216B, is entirely provided by pulsatile-flow pump 124 (even though continuous-flow pump 140 continues to pump constantly). (The flow rate during portion 230 of systole is thus not dependent on the delta pressure across the pump, unlike in conventional LVAD pumps, as described hereinabove with reference to FIG. 7.) Thus, during portion 230 of systole, the pressure increases substantially, as shown in FIGS. 8B-C, with a greater pressure increase than the pressure increase during the same portion of systole caused by a conventional continuous-flow LVAD pump, as shown in FIG. 8A. This increase in pressure results in a substantial increase in AoP during portion 230 of systole and for some time thereafter, as shown in FIGS. 8B-C. This substantial increase in AoP during systole provides substantial aortic pulsatility that mimics the natural aortic pulsatility in a healthy heart, avoiding the alteration of arterial baroreceptors, and resulting potential harmful effects on many organs, which may be caused by conventional continuous-flow LVAD pumps.

During the remainder of the cardiac cycle, typically including the remainder of systole and all of diastole, in which pulsatile-flow pump 124 does not pump blood (as magnetic piston 40 either moves upstream or is stationary), blood flow through LVAD 120, as reflected by flow rate curve 216B, is entirely driven by continuous-flow pump 140. During this portion of the cardiac cycle, reciprocating one-way valve 42 of magnetic piston 40 of pulsatile-flow pump 124 is open, as is stationary one-way outflow valve 22, if provided. As a result, left ventricle 92 comes into fluid communication with ascending aorta 96 via continuous-flow pump 140 and the open valve(s) of pulsatile-flow pump 124, and LVAD 120 thus behaves as a conventional continuous-flow pump, i.e., the flow rate is driven largely by the delta pressure across the pump, i.e., the difference between AoP and LVP, in accordance with pump curve 200 (for the given pump speed), as described hereinabove with reference to FIG. 7.

Typically, the portion 230 of systole in which pulsatile-flow pump 124 pumps blood has a duration of 200-400 milliseconds, e.g., 300-400 milliseconds, such as 300-350 milliseconds, and/or a duration of 20%-40% of a total duration of the cardiac cycle, e.g., 30%-40%, e.g., 30%-35% of the total duration of the cardiac cycle.

Reference is still made to FIGS. 8B-C. For some applications:
- pulsatile-flow pump 124 is configured to pump 1-2 lpm, e.g., 1.25-1.75 lpm, e.g., 1.5 lpm, and/or
- continuous-flow pump 140 is configured to pump 2.5-10 lpm, e.g., 3-6 lpm, e.g., 5 lpm.

Reference is made to FIG. 8B. For some applications, such as shown in FIG. 8B, the control circuitry is configured, during each of the cardiac cycles, to activate pulsatile-flow pump 124 to begin the portion 230 of systole at or near the beginning of systole, e.g., 0-50 milliseconds after the beginning of systole (at the Q deflection of the QRS complex).

Reference is still made to FIG. 8B. At a point 231 during systole at which tubular linear motor of 44 pulsatile-flow pump 124 completes its downstream stroke (upon conclusion of portion 230 of systole), the delta pressure is quite large, as indicated by a systolic delta arrow 220B in FIG. 8B. As a result of this high delta, continuous-flow pump 140 substantially cannot pump blood and the flow drops substantially (and typically steeply) at a portion 232 of flow rate curve 216B, until the pressure delta declines and continuous-flow pump 140 begins to pump blood, resulting in a fairly steep increase in flow after portion 232.

Reference is made to FIG. 8C. Alternatively, for some applications, such as shown in FIG. 8C, the control circuitry is configured, during each of the cardiac cycles, to activate pulsatile-flow pump 124 to begin the portion 230 of systole later during systole, i.e., at a later point 233 during systole. For example, the control circuitry may be configured to activate pulsatile-flow pump 124 to begin the portion 230 of systole at a pre-set or a calculated amount of time after the beginning of systole. For example, the control circuitry may be configured to activate pulsatile-flow pump 124 to begin the portion 230 of systole at a delay after the beginning of systole, the delay typically having:
- a duration of 200-400 milliseconds, e.g., 300-400 milliseconds, such as 300-350 milliseconds, and/or
- a duration equal to 20%-40% of a total duration of the cardiac cycle, e.g., 30%-40%, e.g., 30%-35% of the total duration of the cardiac cycle (e.g., as estimated based on previous recent cardiac cycles, as ascertained using cardiac sensor 52).

Alternatively, for some applications, the control circuitry is configured to activate pulsatile-flow pump 124 to begin the portion 230 of systole shortly before, at, or shortly after peak blood flow during systole. For example, the control circuitry may be configured to activate pulsatile-flow pump 124 to begin the portion 230 of systole between 50 milliseconds (e.g., 25 milliseconds) before and 50 milliseconds (e.g., 25 milliseconds) after peak blood flow during systole.

Further alternatively, for some applications, the control circuitry is configured to activate pulsatile-flow pump 124 to begin the portion 230 of systole upon detection (e.g., 0-25 milliseconds after detection) by the control circuitry of a beginning of a decline in pressure after a rise in pressure during systole. To this end, such as shown in FIG. 6B, the LVAD system typically comprises an upstream pressure sensor, which is disposed and configured to measure blood pressure of blood upstream of magnetic piston 40 of pulsatile-flow pump 124. For example, the blood pressure sensor may comprise:
- upstream pressure sensor 82A, described hereinabove with reference to FIG. 2, which is disposed and configured to measure blood pressure of blood entering upstream inflow end 28 of pump chamber 26 of pulsatile-flow pump 124,
- an upstream pressure sensor 82C, which is disposed along tube 146 (which couples second inlet 142B of pulsatile-flow pump 124 in the fluid communication with first outlet 144A of continuous-flow pump 140), and which is configured to measure blood pressure of blood entering upstream inflow end 28 of pump chamber 26 of pulsatile-flow pump 124, or
- an upstream pressure sensor 82D, which is disposed upstream of continuous-flow pump 140, and configured to measure left-ventricular pressure (LVP); for example, upstream pressure sensor 82D may be coupled to inflow cannula 138.

(Although all three pressure sensors 82A, 82C, and 82D are shown in FIG. 6B, in practice the LVAD system typically comprises only one of these sensors in configurations in which upstream blood pressure is measured.)

Even though upstream pressure sensors 82A and 82C, on the one hand, and upstream pressure sensor 82D, on the other hand, measure different pressures from each other, the above-mentioned decline in pressure occurs at substantially the same time in both pressures.

Reference is again made to FIG. 8C. As described above regarding the timing of activation of pulsatile-flow pump 124 described hereinabove with reference to FIG. 8B, at point 231 during systole at which tubular linear motor 44 of pulsatile-flow pump 124 completes its downstream stroke (upon conclusion of portion 230 of systole), the delta pressure is quite large, as indicated by systolic delta arrow 220B in FIG. 8B, as well as in FIG. 8C. As a result of this high delta, continuous-flow pump 140 substantially cannot pump blood and the flow drops substantially (and typically steeply) at portion 232 of flow rate curve 216B labeled in FIG. 8B, until the pressure delta declines and continuous-flow pump 140 begins to pump blood. By contrast, in the timing of pulsatile-flow pump 124 illustrated in FIG. 8C, the drop in flow coincides with the natural drop in flow toward the end of systole. As a result, the portion 232 of flow rate curve 216B shown in FIG. 8B is substantially subsumed by the natural drop, and the fairly steep increase in flow after portion 232 of FIG. 8B is absent in FIG. 8C.

The different beginning-point techniques may be implemented in combination. For example, the control circuitry is configured to activate pulsatile-flow pump 124 to begin the portion 230 of systole upon the detection by the LVAD system of the beginning of the decline in the pressure after the rise in the pressure during systole, provided that this decline occurs at the pre-set or the calculated amount of time after the beginning of systole, as described above.

As described above, LVAD 120 advantageously improves aortic pulsatility compared to conventional continuous-flow LVAD pumps. In addition, in LVAD 120, unlike conventional continuous-flow LVAD pumps, malfunction of the continuous-flow pump cannot result in death, because, even in the event of such malfunction, pulsatile-flow pump 124 continues to pump blood. Optionally, LVAD is configured to increase the blood flow provided by pulsatile-flow pump 124 in the event of failure of continuous-flow pump 140.

In addition, LVAD 120 may have several advantages compared to LVAD 20, described hereinabove with reference to FIGS. 1-5D. Pulsatile-flow pump 124 of LVAD 120 typically requires a smaller stroke volume than pulsatile-flow pump 24 of LVAD 20, because continuous-flow pump 140 provides a portion of the blood flow of each cardiac cycle, when pulsatile-flow pump 124 is not pumping, as described above. Therefore, pulsatile-flow pump 124 can be smaller than pulsatile-flow pump 24, and typically consumes less power. This smaller size may simplify and/or otherwise facilitate implantation of pulsatile-flow pump 124.

In addition, LVAD 120 can be implanted using the same conventional techniques used for implanting conventional continuous-flow LVAD pumps, because:
continuous-flow pump 140, including inflow cannula 138, may be implantable and attachable to apex 94 of left ventricle 92 at second site 36B using conventional LVAD implantation techniques, and
outflow cannula 32 may be coupled in fluid communication with circulatory system 34 at first site 36A using conventional LVAD implantation techniques.

Pulsatile-flow pump 124 of LVAD 120 is effectively disposed along the outflow cannula of the continuous-flow pump, such that the presence of the pulsatile-flow pump does not materially alter the conventional implantation procedure with which cardiac surgeons are familiar. Optionally, the outflow cannula of continuous-flow pump 140 is provided to the surgeon with pulsatile-flow pump 124 disposed along the cannula. Continuous-flow pump 140 may provided to the surgeon disconnected from the cannula, and the surgeon may connect the cannula, including pulsatile-flow pump 124, to continuous-flow pump 140. Alternatively, pulsatile-flow pump 124 is pre-coupled in fluid communication to continuous-flow pump 140 during manufacture.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A left ventricular assist device (LVAD) system for treating a patient, the LVAD system comprising:
   (i) an implantable LVAD for implantation in the patient, the LVAD comprising:
   (a) an outflow cannula, which is couplable in fluid communication with a circulatory system of the patient at a first site;
   (b) an inflow cannula, which is couplable in fluid communication with the circulatory system at a second site upstream of the first site;
   (c) a continuous-flow pump, which comprises (1) a first inlet in fluid communication with the inflow cannula, and (2) a first outlet; and
   (d) a pulsatile-flow pump, which comprises (1) a second inlet in fluid communication with the first outlet of the continuous-flow pump, and (2) a second outlet in fluid communication with the outflow cannula; and
   (ii) control circuitry, which is configured to:
   activate the continuous-flow pump to provide flow without synchronization with cardiac cycles of a heart of the patient, and
   activate the pulsatile-flow pump to provide pulsatile flow synchronized with the cardiac cycles.

2. The LVAD system according to claim 1, further comprising a cardiac sensor, which is configured to sense one or more features of the cardiac cycles, wherein the control circuitry is coupled to the cardiac sensor.

3. The LVAD system according to claim 1, wherein the second site is an apex of a left ventricle of the heart.

4. The LVAD system according to claim 1, further comprising a stationary one-way outflow valve, which is arranged to allow downstream blood flow from the second outlet of the pulsatile-flow pump to the outflow cannula, and to inhibit upstream blood flow from the outflow cannula to the second outlet.

5. The LVAD system according to claim 1, further comprising a tube which couples the second inlet of the pulsatile-flow pump in the fluid communication with the first outlet of the continuous-flow pump.

6. The LVAD system according to claim 1, wherein the pulsatile-flow pump:

is shaped so as to define a pump chamber having (a) an upstream inflow end in fluid communication with the second inlet, and (b) a downstream outflow end in fluid communication with the second outlet, and comprises a tubular linear motor, which comprises (a) a magnetic piston, which comprises a reciprocating one-way valve configured to allow downstream blood flow and inhibit upstream blood flow; and (b) a stator, which is configured to magnetically drive the magnetic piston with reciprocating motion, so as to pump blood downstream during downstream motion of the magnetic piston while the reciprocating one-way valve is closed.

7. The LVAD system according to claim 6, wherein the control circuitry is configured to activate the tubular linear motor to provide the pulsatile flow synchronized with the cardiac cycles by, during each of the cardiac cycles:

activating the stator of the tubular linear motor to move the magnetic piston downstream during a portion of systole of the cardiac cycle, and activating the stator of the tubular linear motor to move the magnetic piston upstream during at least a portion of diastole of the cardiac cycle.

8. The LVAD system according to claim 6, further comprising a stationary one-way outflow valve, which is arranged to allow downstream blood flow from the second outlet of the pulsatile-flow pump to the outflow cannula, and to inhibit upstream blood flow from the outflow cannula to the second outlet.

9. The LVAD system according to claim 6, further comprising a stationary one-way inflow valve, which is arranged to allow downstream blood flow into the pump chamber of the pulsatile-flow pump, and to inhibit upstream blood flow from the pump chamber.

10. The LVAD system according to claim 1, wherein the continuous-flow pump comprises a magnetically-levitated centrifugal pump.

11. The LVAD system according to claim 1, wherein the control circuitry is configured to activate the pulsatile-flow pump to provide pulsatile flow synchronized with the cardiac cycles by, during each of the cardiac cycles, activating the pulsatile-flow pump to pump blood downstream during a portion of systole of the cardiac cycle.

12. The LVAD system according to claim 11, wherein the control circuitry is configured to activate the pulsatile-flow pump to pump blood downstream during the portion of systole of the cardiac cycle, and not to pump blood downstream during any portion of diastole of the cardiac cycle.

13. The LVAD system according to claim 11, wherein the control circuitry is configured, during each of the cardiac cycles, to activate the pulsatile-flow pump to begin the portion of systole at a delay after the beginning of systole.

14. The LVAD system according to claim 13, wherein a duration of the delay is 200-400 milliseconds.

15. The LVAD system according to claim 13, further comprising a cardiac sensor, which is configured to sense one or more features of the cardiac cycles, wherein the control circuitry is coupled to the cardiac sensor, and wherein the control circuitry is configured to set a duration of the delay equal to 20%-40% of a total duration of the cardiac cycle.

16. The LVAD system according to claim 13, wherein the control circuitry is configured to activate the pulsatile-flow pump to begin the portion of systole upon detection by the control circuitry of a beginning of a decline in pressure after a rise in pressure during systole.

17. The LVAD system according to claim 16, wherein the pulsatile-flow pump:

is shaped so as to define a pump chamber having (a) an upstream inflow end in fluid communication with the second inlet, and (b) a downstream outflow end in fluid communication with the second outlet, and comprises a tubular linear motor, which comprises (a) a magnetic piston, which comprises a reciprocating one-way valve configured to allow downstream blood flow and inhibit upstream blood flow; and (b) a stator, which is configured to magnetically drive the magnetic piston with reciprocating motion, so as to pump blood downstream during downstream motion of the magnetic piston while the reciprocating one-way valve is closed, wherein the LVAD system further comprises an upstream pressure sensor, which is disposed and configured to measure blood pressure of blood upstream of the magnetic piston of the pulsatile-flow pump, and wherein the control circuitry is configured to detect the beginning of the decline in the pressure after the rise in the pressure during systole, using the upstream pressure sensor.

18. The LVAD system according to claim 17, wherein the upstream pressure sensor is disposed and configured to measure the blood pressure of blood entering the upstream inflow end of the pump chamber of the pulsatile-flow pump.

19. The LVAD system according to claim 17, wherein the upstream pressure sensor is disposed upstream of the continuous-flow pump, and configured to measure left-ventricular pressure (LVP).

20. A method for treating a patient comprising:

implanting a left ventricular assist device (LVAD) of an LVAD system in the patient, by:

coupling an outflow cannula of the LVAD in fluid communication with a circulatory system of the patient at a first site; and coupling an inflow cannula of the LVAD in fluid communication with the circulatory system at a second site upstream of the first site, wherein the LVAD includes (a) a continuous-flow pump, which includes (1) a first inlet in fluid communication with the inflow cannula, and (2) a first outlet, and (b) a pulsatile-flow pump, which includes (1) a second inlet in fluid communication with the first outlet of the continuous-flow pump, and (2) a second outlet in fluid communication with the outflow cannula; and activating control circuitry of the LVAD system to:

activate the continuous-flow pump to provide flow without synchronization with cardiac cycles of a heart of the patient, and activate the pulsatile-flow pump to provide pulsatile flow synchronized with the cardiac cycles.

\* \* \* \* \*